United States Patent [19]

von Bebenburg et al.

[11] E Re. 31,071

[45] Reissued Nov. 2, 1982

[54] 6-AZA-3H-1,4-BENZODIAZEPINES

[75] Inventors: Walter von Bebenburg, Buchschlag; Heribert Offermanns, Grossauheim, both of Fed. Rep. of Germany

[73] Assignee: Deutsche Gold- und Silber-Scheideanstalt vormals Roessler, Frankfurt, Fed. Rep. of Germany

[21] Appl. No.: 298,513

[22] Filed: Sep. 1, 1981

Related U.S. Patent Documents

Reissue of:

[64] Patent No.: 4,008,223
Issued: Feb. 15, 1977
Appl. No.: 507,605
Filed: Sep. 19, 1974

U.S. Applications:

[63] Continuation-in-part of Ser. No. 313,542, Dec. 8, 1972, abandoned.

[30] Foreign Application Priority Data

Dec. 9, 1971 [AT] Austria ..... 10604/71
Mar. 20, 1974 [AR] Argentina ..... 252867

[51] Int. Cl.[3] ..... C07D 471/04

[52] U.S. Cl. ..... 260/239.3 B; 546/194; 546/312; 544/124; 544/279; 424/256; 424/248.54

[58] Field of Search ..... 260/239.3 B

[56] References Cited

U.S. PATENT DOCUMENTS

| | | | |
|---|---|---|---|
| 2,893,992 | 7/1959 | Sternbach | 260/239 BD |
| 3,296,249 | 1/1961 | Bell | 260/239.3 D |
| 3,299,053 | 1/1967 | Archer et al. | 260/239.3 D |
| 3,304,313 | 2/1967 | McMillan et al. | 260/239.3 D |
| 3,314,941 | 4/1967 | Littell et al. | 260/239.3 D |
| 3,371,085 | 2/1968 | Reeder et al. | 260/239.3 D |
| 3,422,091 | 1/1969 | Archer et al. | 260/239.3 |
| 3,445,458 | 5/1969 | Bell | 260/239.3 D |
| 3,694,552 | 9/1972 | Hester | 260/239 BD |

OTHER PUBLICATIONS

Littell et al., "J. Med. Chem.", vol. 8, pp. 722–724 (1965).

*Primary Examiner*—Robert T. Bond
*Attorney, Agent, or Firm*—Cushman, Darby & Cushman

[57] ABSTRACT

There are produced 6-aza-3H-1,4-benzodiazepines and 6-aza-1,2-dihydro-3H-1,4-benzodiazepines of the formula

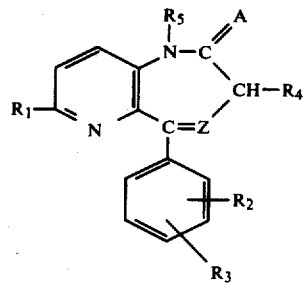

where $R_1$ is a halogen, $R_2$ and $R_3$ are hydrogen, halogen, trifluoromethyl, nitro, nitrile, hydroxy, lower alkyl, lower alkoxy, $R_4$ is hydrogen, hydroxyl, hydroxyl acylated with a mono or dicarboxylic aid of 2 to 6 carbon atoms, lower alkoxy, lower alkyl, benzyl, lower aliphatic acyl, carboxy or carb-lower alkoxy, Z is nitrogen or NO, $R_5$ is hydrogen, lower alkyl, lower alkyl substituted with cycloalkyl of 3 to 6 carbon atoms, lower alkenyl, cycloalkyl of 3 to 6 carbon atoms, lower hydroxyalkyl, benzyl, aliphatic acyl of 2 to 6 carbon atoms aminoalkyl of 2 to 7 carbon atoms, mono or di lower alkyl substituted aminoalkyl of 2 to 7 carbon atoms, lower alkyl substituted with 5 to 7 membered N-heterocyclic ring, containing 0 to 1 additional nitrogen or oxygen atoms, and A is oxygen, sulfur, $=NR_5$, $=NOR_5$, $=NH—NHR_5$ or two hydrogen atoms and the $—N(R_5)—C—(=A)—$ can also be in the tautomeric form $—N=C(AR_5)$ 13 and pharmacologically acceptable salts thereof. The compounds have spasmolytic, antiphlogistic and tranquilizer activity.

15 Claims, No Drawings

6-AZA-3H-1,4-BENZODIAZEPINES

Matter enclosed in heavy brackets [ ] appears in the original patent but forms no part of this reissue specification; matter printed in italics indicates the additions made by reissue.

This is a continuation-in-part application of Ser. No. 313,542, filed Dec. 8, 1972 and now abandoned.

The invention is concerned with new 6-aza-3H-1,4-benzodiazepines and 6-aza-1,2-dihydro-3H-1,4-benzodiazepines of the formula:

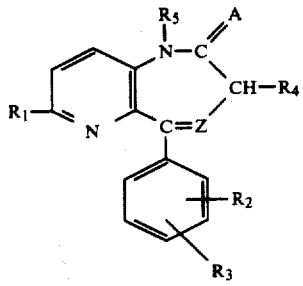

where $R_1$ is a halogen, $R_2$ and $R_3$ are hydrogen, halogen, trifluoromethyl, nitro, nitrile, hydroxy, lower alkyl, lower alkoxy, $R_4$ is hydrogen, hydroxyl, hydroxyl acylated with a mono or dicarboxylic acid of 2 to 6 carbon atoms, lower alkoxy, lower alkyl, benzyl, lower aliphatic acyl, carboxy or carb-lower alkoxy, Z is nitrogen or NO, $R_5$ is hydrogen, lower alkyl, lower alkyl substituted with cycloalkyl of 3 to 6 carbon atoms, lower alkenyl, cycloalkyl of 3 to 6 carbon atoms, lower hydroxyalkyl, benzyl, aliphatic acyl of 2 to 6 carbon atoms, aminoalkyl of 2 to 7 carbon atoms, mono or di lower alkyl substituted aminoalkyl of 2 to 7 carbon atoms, lower alkyl substituted with 5 to 7 membered N-heterocyclic ring, containing 0 to 1 additional nitrogen or oxygen atoms, and A is oxygen, sulfur, $=NR_5$, $=NOR_5$, $=NH—NHR_5$ or two hydrogen atoms and the $—N(R_5)—C—(=A)—$ can also be in the tautomeric form $—N=C(AR_5)—$ and pharmacologically acceptable salts thereof.

There can be prepared for example salts with acids such as hydrochloric acid, hydrobromic acid, succinic acid, tartaric acid, fumaric acid, sulfuric acid, citric acid, phosphoric acid, lactic acid, malonic acid, maleic acid, acetic acid, propionic acid, p-toluenesulfonic acid.

In the compounds of formula I the halogen atoms can have an atomic weight of 9 to 80, i.e. they can be chlorine, fluorine or bromine, preferably chlorine and fluorine. As the above name lower alkyl, alkenyl, alkoxy, hydroxyalkyl and carbalkoxy groups there can be employed those containing 1 to 6 carbon atoms, preferably 1 to 4 carbon atoms. The aminoalkyl group can contain 2 to 7 carbon atoms and can be straight or branched chain. Preferably the aminoalkyl group contains 2 to 5 carbon atoms. The aliphatic acyl groups contain 2 to 6 carbon atoms. Saturated acyl groups are preferred. As dicarboxylic acid there are especially employed those containing 3 to 6 carbon atoms, preferably 3 to 5 carbon atoms. Examples of these are malonic acid, succinic acid, glutaric acid and adipic acid. The alkyl groups as such or as constituents of other groups can be either straight chain or branched. Examples are methyl, ethyl, propyl, isopropyl, butyl, tert. butyl, hexyl, isobutyl, hexyl, cyclopropyl, cyclopentyl, cyclohexyl, cyclohexyl propyl, cyclopropylmethyl, cyclohexylpentyl, methoxy, ethoxy, propoxy, isopropoxy, butoxy, isobutoxy, tert. butoxy, amyloxy, hexyloxy, hydroxymethyl, hydroxyethyl, hydroxypentyl, dimethylamino, diethylamino, dibutylamino, carbmethoxy, carbethoxy, carbpropoxy, carbpentoxy, acetyl, propionyl, butyryl, pentanoyl, isovaleroyl, isobutyryl, cyclobutylmethyl, allyl, butenyl-(2), piperidinoethyl morpholinoethyl.

In addition to the compounds mentioned in the working examples other compounds within the present invention include 5-phenyl-6-aza-7-fluoro-1,2-dihydro-3H-1,4-benzodiazepinone-(2); 5-phenyl-6-aza-7-bromo-1,2-dihydro-3H-1,4-benzodiazepinone-(2); 5-phenyl-6-aza-7-fluoro-1,2-dihydro-3H-1,4-benzodiazepinone-(2)-4 oxide; 5-(o-trifluoromethylphenyl)-6-aza-7-chloro-1,2-dihydro-3H-1,4-benzodiazepinone-(2); 5-(p-fluorophenyl)-6-aza-7-bromo-1,2-dihydro-3H-1,4-benzodiazepinone-(2); 5-(o-bromophenyl)-6-aza-7-bromo-1,2-dihydro-3H-1,4-benzodiazepinone-(2); 5-(m-nitrophenyl)-6-aza-(7-chloro-1,2-dihydro-3H-1,4-benzodiazepinone-(2); 5-(o-hydroxyphenyl)-6-aza-7-chloro-7-chloro-1,2-dihydro-3H-1,4-benzodiazepinone-(2); 5-(2'4'-dihydroxyphenyl)-6-aza-7-fluoro-1,2-dihydro-3H-1,4-benzodiazepinone-(2); 5-(p-butylphenyl)-6-aza-7-chloro-1,2-dihydro-3H-1,4-benzodiazepinone-(2); 5-(2',4'-dimethylphenyl)-6-aza-7-chloro-1,2-dihydro-3H-1,4-benzodiazepinone-(2); 5-(p-methoxyphenyl)-6-aza-7-chloro-1,2-dihydro-3H-1,4-benzodiazepinone-(2); 5-(p-hexylphenyl)-6-aza-7-chloro-1,2-dihydro-3H-1,4-benzodiazepinone-(2); 1-caproyl-3-caproxy-5-phenyl-6-aza-7-chloro-1,2-dihydro-3H-1,4-benzodiazepinone-(2); 1-malonoyl-3-malonoxy-5-(o-bromophenyl)-6-aza-7-chloro-1,2-dihydro-3H-1,4-benzodiazepinone-1(2); 1-butyryl-3-butyroxy-5-(phenyl)-6-aza-7chloro-1,2-dihydro-3H-1,4-benzodiazepinone; 5-(o-cyanophenyl)-6-aza-7-chloro-1,2-dihydro-3H-1,4-benzodiazepinone-(2); 5-(2-chloro-4-methylphenyl)-6-aza-7-chloro-1,2-dihydro-3H-1,4-benzodiazepinone-(2); 5-phenyl-6-aza-7-chloro-1,2-dihydro-3H-1,4-benzodiazethiopinone-(2).

The compounds of the invention have valuable pharmacodynamic properties. For example, they possess psychosedative and especially anxiolytic (tranquilizer) properties. Furthermore they have an antiphlogistic activity.

The compounds can be prepared by methods which are known in themselves such as a. condensing a compound of the formula

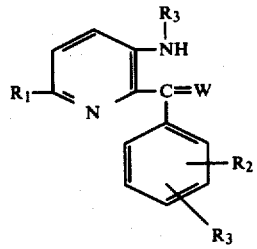

II where $R_1$, $R_2$, $R_3$ and $R_5$ are as defined above and W is either an oxygen atom or the group=NH or=NOH with a compound of the formula

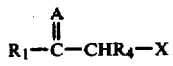

III where $R_4$ is as defined above, A is oxygen or sulfur or two hydrogen atoms or the group $=NR_5$ and $R_7$ is a hydroxy group, a halogen atom (of atomic weight 9 to 80), a lower alkoxy group, a mercapto group, a lower alkylmercapto group, an amino group or a lower alkylamino group, the structural element $-C(=A)R_7$ collectively can also be a nitrile group and x is an amino group or a halogen atom, in a given case with addition of an acid binding agent, e.g. triethylamine, whereby it can be worked up in the presence of ammonia or an ammonium derivative in the case where W is O and X is halogen and the reaction product is treated in a given case finally in an alkaline medium, or b. in a compound of Formula I one or more of the symbols $R_5$, $R_4$, A and Z can be changed into another compound of corresponding meaning;

c. and in a given case the product obtained according to process (a) or (b) is acylated through aliphatic acids or acid derivatives having 2 to 6 carbon atoms in the 1-, 2-, and/or 3-positions.

Process (a) is carried out in the conventional solvents or suspension agents at temperatures between 0° and 200° C., preferably 20° to 150° C. Especially there can be employed polar solvents, for example alcohols, e.g. methyl alcohol, ethyl alcohol, isopropyl alcohol, propyl alcohol and butyl alcohol, dioxane, tetrahydrofurane, dimethyl sulfoxide, dimethyl formamide and similar materials. When W is O there can also be used pyridine and quinoline. In a given case there are suitably added acidic or basic materials, as for example, piperidine or aliphatic carboxylic acids, e.g. acetic acid and propionic acid. When x is a halogen atom there are suitably employed basic materials which effect acid splitting, e.g. triethylamine. When $R_7$ is a hydroxy group (in this case the structural unit $-(=A)R_7$ for example, can make a carboxyl group) the addition of special customary water splitting off agents such as dicyclohexylcarbodiimide is suitable or in some cases necessary.

When there are used compounds of the formula III where A is two hydrogen atoms, $R_7$ is chlorine or bromine, the remaining symbols which have the meanings already set forth (in case X is an amino group that is preferably blocked through protective groups) the process can be carried out as follows. A compound of formula II wherein $R_5$ is hydrogen and W is oxygen, $R_2$, $R_3$ and $R_1$ have the meanings set forth above, is acylated with an aliphatic acid halide, e.g. acetyl chloride, acetyl bromide or propionyl chloride, an aliphatic acid ester, e.g. methyl acetate, ethyl acetate or propyl acetate, an aliphatic acid anhydride, e.g. acetic anhydride, an aliphatic ketene, e.g. ketene itself or benzoyl chloride in an inert solvent such as dioxane, benzene, tetrahydrofurane or dimethyl formamide at a temperature between 0° and 150° C. The compound obtained after conversion to the alkali salt (e.g. with sodium hydride or sodamide) is reacted with a compound of formula III above (for example in a nonbasic solvent such as dioxane, dimethyl formamide or dimethyl sulfoxide between 0° and 200° C.). Subsequently the acyl group which is on the nitrogen atom in the 3 position of the pyridine ring can be split off in an acid or basic medium, whereby in a given case there simultaneously takes place ring closing to compounds of formula I.

Frequently process (a) can also be carried out so that the amino group in the 5-position of formula II and/or the amino group of formula III ($X=NH_2$) has a similar protective group. Frequently such protective groups are required for the production of the starting compounds.

In many cases the splitting off of such a protective group takes place simultaneously with the cyclization.

These protective groups are easily split off. There are employed either easily solvolytically splittable acyl groups or groups splittable by hydrogenation, as for example, the benzyl radical. The solvolytically splittable protective groups are split off for example, by saponification with dilute acids or by means of basic substances (potash, soda, aqueous alkali solutions, alcoholic alkali solutions, $NH_3$) at room temperature or with a short boiling. Hydrogenizably splittable groups such as the benzyl group or the carbobenzoxy radical are suitably split off by catalytic hydrogenation in the presence of customary hydrogenation catalysts, especially palladium catalysts, in a solvent or suspension agent, in a given case under elevated pressure. As solvents or suspension agent there can be used water, lower aliphatic alcohols such as methyl alcohol, ethyl alcohol, isopropyl alcohol, butyl alcohol, cyclic ethers such as dioxane or tetrahydrofurane, aliphatic ethers, e.g. diethyl ether, dimethyl formamide, etc. as well as mixtures of these materials.

As protective groups for the amino group there can be used for example, the benzyl group, α-phenylethyl group, benzyl groups substituted in the benzene nucleus as for example, the p-bromo or p-nitrobenzyl group, the carbobenzoxy group, the carbobenzthio group, the trifluoroacetyl, the phthalyl radical, the trityl radical, the p-toluenesulfonyl radical and similar groups as well as simple acyl groups such as the acetyl group, formyl group, tert. butylcarboxy group, etc. There can be employed especially the protective groups used in the synthesis of peptides and the splitting processes customarily employed in that process. Among others for this purpose reference is made to Jesse P. Greenstein and Milton Winitz "Chemistry of Amino Acids", John Wiley and Sons, Inc. New York (1961) Vol. 2, pages 883 et seq. Also there can be used carbalkoxy groups (for example of low molecular weight such as carbmethoxy, carbethoxy and carbpropoxy).

Process (a) can also be carried out under some circumstances so that before the true cyclization there is isolated previously the intermediate product of the formula:

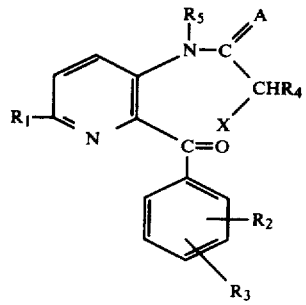

IV

This product can then be cyclized in purified form or as it accumulates. For this purpose there are used temperatures between −70° and +150° C., preferably 0° to 150° C. As solvents or suspending media besides those given above there can be used glacial acetic acid, lower aliphatic alcohols such as methanol and ethanol, acetic anhydride, polyphosphoric acid, aliphatic ethers, e.g.

diethyl ether, chloroform etc. This cyclization can be carried out in a given case using acid condensation agents such as sulfuric acid, hydrochloric acid, hydrobromic acid, toluene sulfonic acid or polyphosphoric acid or basic condensation agents such as pyridine or tertiary amines.

When X is a halogen atom the cyclization is carried out in the presence of ammonia (for example liquid ammonia), whereupon there can also be present tertiary none quaternizing amines, for example, sterically hindered amines such as diisopropylethyl amine or 1,8-bis(-dimethylamino) naphthalene. The halogen atoms employed are chlorine, bromine or iodine. In place of ammonia or additionally to ammonia there can also be used, for example, other derivatives of ammonia which replace a halogen atom by the group $NH_2$, for example, urotropine, alkaliamide, e.g. sodamide or acid amide, in which the acid radical produces a customary protective group as set forth above, and is easily splittable.

When urotropine (hexamethylenetetramine) is used the proces can be carried out as follows: Boiling in chloroform (½ to 8 hours) and splitting off the separated urotropine compound with aqueous or aqueous-alcoholic inorganic acids (e.g. HCl or $H_2SO_4$) at temperatures between, for example, 20° and 150° C.

If acid amides are used it is recommended that there be used condensation agents such as sodium, alkali hydrides, e.g. sodium hydride, alkali amides (especially sodamides), Grignard compounds, lithium alkyls (e.g. butyl lithium) or in special cases, as with tosyl amides, there can be used weaker bases such as $K_2CO_3$, powdered NaOH or potassium hydroxide. As solvents above all dimethylsulfoxide and dimethyl formamide are suitable. There can also be used dioxane, tetrahydrofurane, alcohols, e.g. methyl alcohol, ethyl alcohol and isopropyl alcohol and ethers, e.g. diethyl ether. In using acid amides generally from the intermediate compound IV first there are obtained compounds of formula IV in which x is an amino group protected by the corresponding acid radical. The cyclization then takes place simultaneously with or after splitting off of the protective group. In acid splitting off of the protective group it is generally possible to isolate the compounds of formula IV in which X is the amino group as either the salt or as the free base.

Where a starting material of formula II is used in process (a) in which $R_5$ is an acyl group this can be solvolitically split off in a given case after the end of the reaction according to the conditions mentioned previously, e.g. at page 9, line 13 to page 10, line 22. However, it is also possible, if a pure aliphatic acyl group is employed, to reduce this to an alkyl group (for example by means of complex alkali hydrides such as $LiAlH_4$).

It can happen that in the cyclization according to process (a) there is not formed the 7-membered ring compound but partially or exclusively the 6-membered ring compound of the formula:

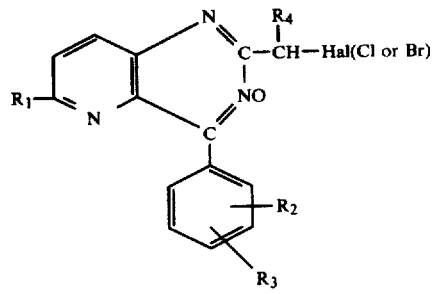

where Hal is chlorine or bromine. In this case a subsequent treatment in an alkaline medium is necessary. This is generally carried out in polar media such as lower alcohols (methanol, ethanol, tertiary butyl alcohol), chloroform, dioxane, etc. at temperatures between 0° and 150° C. As the alkaline medium there can be used, for example, aqueous or alcoholic, especially methanolic or ethanolic NaOH or KOH, in a given case in admixture with the above mentioned solvents; the same reagents in solid, powdered form, also potash as well as aqueous solutions of tertiary amines, above all those which are not quaternized such as diisopropyl methyl amine. There are also be used alkaline ion exchanges, e.g. chloromethylated polystyrene quaternized with trimethylamine, in column form or in suspension.

In this ring expansion there are formed compounds in which the group —N($R_5$)C(=A)— in formula I has the following structures:

—N—C(OH)—, —N=C($NHR_5$)—, —N=C($OR_5$)—, —N=C($NHR_5$—$NHR_5$)— or —N=C($NR_5R_5$)—.

In the ring expansion of compounds of formula V besides the desired diazepine often there are also formed compounds which are built from compounds of formula V without ring expansion by substitution of the halogen atoms by the particular coreactant. The desired compound can then be separated from this and, in a given case, other byproducts also by fractional crystallization or by chromatography in known manner.

According to process (b) azabenzodiazepines of formula I can be substituted or further reacted in suitable manner. For example, compounds of formula I where $R_5$ is a hydrogen atom can be alkylated on the nitrogen atom in known manner. As alkylating agents there can be used, for example, esters of the formula $R_5Hal$, $ArSO_2OR_5$ and $SO_2(OR_5)_2$ wherein Hal is a halogen atom (especially chlorine, bromine or iodine) and Ar is an aromatic radical which, in a given case, is a phenyl or naphthyl radical substituted by one or more lower alkyl groups, e.g. methyl or ethyl, and $R_5$ with the exception of hydrogen has the above defined meaning. For example, there can be used p-toluenesulfonic acid alkyl esters, e.g. methyl p-toluenesulfonate, and ethyl p-toluenesulfonate, lower dialkyl sulfates, e.g. dimethyl sulfate, diethyl sulfate and dipropyl sulfate and the like. The alkylation reaction can take place, in a given case, with addition of customary acid binding agents such as alkali carbonates, e.g. sodium carbonate and potassium carbonate, pyridine or other customary tertiary amines, at temperatures between 0° and 150° C. in inert solvents such as alcohols, e.g. methyl alcohol, ethyl alcohol and t-butyl alcohol, dioxane, dimethyl formamide, dimethyl sulfoxide, aromatic hydrocarbons, such as benzene, toluene or xylene, or acetone.

The group A in a compound of formula I can also be exchanged in various ways. Thus when A is oxygen, this atom can be replaced by sulfur by means of phosphorus pentasulfide. This reaction takes place in inert solvents such as benzene, toluene, dioxane, pyridine or chlorinated hydrocarbons, e.g chloroform, at temperatures between 0° and 150° C. The sulfur compounds thus obtained (cyclic thioamides) can in turn be reacted in polar medium with alkylamines of the formula $NH_2R_5$ (where $R_5$ is as defined above), e.g. methyl amine, propyl amine, allyl amine, whereupon compounds of formula I are formed in which A is the group=NH or $=NR_5$. The reaction is carried out in polar solvents such as methanol, ethanol or excess amine at temperatures between 0° and 150° C.

Compounds of formula I in which $R_4$ is other than hydrogen can for example be produced in the following manner from compounds of formula I in which $R_4$ is hydrogen and the remaining symbols have the meaning specified above—by alkylation, acylation and oxidation. In the alkylation the reaction takes place with esters of the formula HalR'', $SO_2(OR'')$ or $ArSO_2OR''$ where Hal is a halogen atom, especially Cl, Br or I, Ar is an aromatic radical (especially in a given case a phenyl or naphthyl radical with one or more lower alkyl radicals, e.g. methyl or ethyl) and R'' is an alkyl group with 1 to 6 carbon atoms. Thus there can be used methyl chloride, ethyl bromide, propyl iodide, hexyl chloride, dimethyl sulfate, diethyl sulfate, methyl p-toluene sulfonate, butyl p-toluenesulfonate. (The process conditions are the same as set forth above for introducing the $R_5$ group using esters of the formula $R_5Hal$, $ArSO_2OR_5$ and $SO_2(OR_5)_2$).

The acylation can take place in inert solvents or suspension media such as dioxane, dimethyl formamide, benzene or toluene at temperatures between 0° and 200° C. As acylation agents there can be used ketenes, e.g. ketene itself, acid halides, e.g. acetyl chloride or propionyl bromide, acid anhydrides, e.g. acetic anhydride or acid esters of aliphatic carboxylic acids with 2 to 6 carbon atoms, e.g. mono methyl oxalate, mono ethyl malonate, mono methyl succinate, mono ethyl adipate, or carboxylic acid half ester halides with 1 to 6 carbon atoms, in a given case, with the addition of an acid binding agent such as potassium carbonate or sodium methylate or a tertiary amine, for example, triethylamine. There are especially employed esters with lower aliphatic alcohols, e.g. methyl alcohol, ethyl alcohol, butyl alcohol. In the alkylation and acylation one can also proceed in such a manner that first there is produced from the reacting compound of formula I where $R_4$ is H an alkali compound by reacting with the compound of formula I an alkali metal, alkali hydride or alkali amine (especially sodium or sodium compounds) in an inert solvent such as dioxane, dimethyl formamide, benzene or toluene at temperatures between 0° and 150° C. and then the alkylating or acylating agent is added. As acylating agent in this case there can also be used carbon dioxide whereby compounds of formula I are obtained where $R_4$ is COOH.

In place of the alkylation and acylation agents mentioned there can also be used other chemically equivalent agents (see for example L. F. and Mary Fieser "Reagents for Organic Synthesis", John Wiley and Sons, Inc. New York, 1967 Vol. 1, pages 1303–4 and Vol. 2, page 471). It should be understood that acyl groups present in the compounds of formula I also can be split off again in known manner.

Compounds can be obtained by oxidation in which $R_4$ is a hydroxyl group. For this purpose compounds of formula I in which $R_4$ is a hydrogen can be reacted in inert solvents such as dilute acetic acid, ethyl acetate or acetone with hydrogen peroxide, peracetic acid, perpropionic acid, perbutyric acid, pervaleric acid or other conventional organic peracids. The temperature is preferably between −10° and +70° C.

Compounds of formula I where $R_4$ is a hydroxyl group can also be obtained by treating compounds of formula I in which $R_4$ is H and Z is N→O either in polar solvents such as methanol, methanol-water mixtures, dioxane methanol mixtures, ethanol, etc. with alkali (for example sodium hydroxide, potassium hydroxide) or in low molecular weight aliphatic acid anhydrides (for example acetic anhydride), in a given case in admixture with other inert solvents; thereupon there occurs a rearrangement according to which the oxygen atom on the nitrogen atom forms a hydroxyl group on the adjacent carbon atom. This rearrangement is accomplished at temperatures between 0° and 150° C., especially 0° to 100° C.

Compounds of formula I wherein Z is a nitrogen atom can be converted into the corresponding N-oxide. The reagents and conditions are analogous to those of the hydroxylation of $R_4$. The temperatures generally are somewhat lower, preferably between 0° and 50° C. (otherwise at increase of temperature there occurs the above described rearrangement).

In compounds of formula I where Z is the group NO the oxygen atom can be removed by catalytic hydrogenation, or by chemical deoxygenation. As catalysts for the catalytic hydrogenation there are suitable for example the customary metallic hydrogenation catalysts, especially noble metal catalysts (palladium/activated carbon, platinum) or Raney-nickel; as solvents there are preferably employed lower alcohols, e.g. methanol, ethanol or isopropanol. The temperatures are between 0° and 200° C., preferably between 0° and 100° C. In a given case the process can be carried out at pressures up to 50 atmospheres absolute. For chemical deoxygenation there are preferably used phosporus trichloride or dimethyl sulfoxide in inert solvents such as dioxane, benzene or toluene at temperatures between 0° and 150° C., preferably 0° to 100° C.

Compounds of formula I in which A is an oxygen atom or a sulfur atom can also be converted by reduction into compounds of formula I in which A is two hydrogen atoms. This reduction can be carried out, for example, in a solvent or suspension agent at temperatures between 0° and 100° C. As solvents or suspension agents there can be used, for example, water, lower aliphatic alcohols, e.g. methyl alcohol, ethyl alcohol, isopropyl alcohol or butyl alcohol, cyclic ethers, such as dioxane or tetrahydrofurane, aliphatic ethers, e.g. diethyl ether, dimethyl formamide, tetramethyl urea, etc. as well as mixtures of these agents with each other. Preferably the reduction is undertaken by catalytic hydrogenation. As catalysts there are employed conventional finely divided metal catalysts as, for example, nickel (Raney-nickel) or cobalt (Raney-cobalt). The catalysts can be employed with or without carriers. The process can be carried out at normal pressure or elevated pressure.

This reduction of the keto or the thio group, however, can also take place by metal hydrides or complex metal hydrides such as LiH, $LiAlH_4$, alkali borohydrides, e.g. sodium borohydride sodium triethoxyaluminum hydride or sodium dihydro bis(2-methoxyethoxy) aluminate.

Basic compounds of formula I can be converted in known manner into their salts. As anions for these salts there can be used the known therapeutically usable acid radicals such as those set forth previously.

If the compounds of formula I contain acid groups they can be converted in customary manner into their alkli (e.g. sodium or potassium), ammonium or substituted ammonium salts. As substituted ammonium salts there can be used especially salts of tertiary amines, lower aminoalcohols and bis and tris (hydroxyalkyl) amines. The alkyl group contains 1 to 6 carbon atoms. Examples of such materials are trimethylamine, tributylamine, triethyl amine, tripropyl amine, aminoethanol, aminopropanol, diethanolamine, dibutanol amine, triethanolamine and tripropanolamine.

The free bases of the compounds can be prepared from their salts in customary fashion, for example, by treating a solution in an organic agent such as alcohols, e.g. methanol, with soda or soda lye.

Those compounds of formula I which contain asymmetric carbon atoms and as a rule result as racemates, can be split into the optically active isomers in known manner with the help of an optically active acid. However, it is also possible to employ from the beginning an optically active starting material whereby a correspondingly optically active or diastereomer form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, cremes, powders, liquids, dusts or aerosols. As liquids there can be used, for example, oily or aqueous solutions or suspensions, emulsions, injectable aqueous and oily solutions or suspensions.

For example, there can be made and used in the invention compounds of formula I where the symbols $R_1$ to $R_5$ as well as A and Z have the following meaning:

$R_1$ is chlorine:

$R_2$ is chlorine, fluorine, $CF_3$, CN or alkyl with 1 to 3 carbon atoms, e.g. methyl, ethyl, propyl or isopropyl, preferably methyl, preferably in the ortho or para position, hydrogen. The preferred substituents are hydrogen or fluorine or chlorine in the ortho position;

$R_3$ is hydrogen, fluorine or chlorine with the o-position being preferred;

$R_4$ is hydrogen or an alkyl group with 1 to 6 carbon atoms, e.g. methyl, ethyl, isopropyl, sec. butyl, amyl or hexyl, especially 1 to 3 carbon atoms, or a hydroxy group or the carboxy group. Especially H or the hydroxy group or the acylated hydroxy preferred;

$R_5$ is the benzyl group or an alkyl or alkenyl group with 1 to 4 carbon atoms, e.g. methyl, ethyl, propyl, isopropyl, butyl, t-butyl, allyl, methallyl, crotyl or butenyl-2 (preferably methyl, isopropyl, allyl or butenyl-2), or an oxyalkyl group with 2 to 6 carbon atoms, e.g. hydroxyethyl, hydroxypropyl, 4-hydroxybutyl, 2-hydroxyhexyl, especially with 2 to 4 carbon atoms. Preferably $R_5$ is an oxyethyl group or a dialkylaminoethyl or dialkylaminopropyl or dialkylaminoisopropyl or a morpholino alkyl or piperidinoalkyl wherein the alkyl radical preferably contains 1 to 4 carbon atoms (for example the diethylaminoethyl group, morpholinoethyl or piperidinoethyl group) or the cyclopropylmethyl-, cyclobutyl methyl-, cyclopentyl methyl) or the cyclohexylmethyl group. Preferably $R_5$ is H or a lower alkyl group with 1 to 4 carbon atoms, for example, methyl;

A is especially oxygen and also is sulfur or two hydrogen atoms or the group=NH, $=NR_5$ or $=NHR'_5$ or in the tautomeric form together with $R_5$, $-SR'_5$, $-NHR'_5$ or $-N(R'_5)_2$ where $R'_5$ is a lower alkyl group having 1 to 3 carbon atoms, especially methyl or ethyl;

Z is nitrogen or NO.

Especially favorable activity is possessed by compounds of formula I, where $R_1$ is chlorine, $R_2$ and $R_3$ are the same or different and are hydrogen, fluorine or chlorine, preferably in the ortho position, A is an oxygen atom and Z is a nitrogen atom, $R_4$ is hydrogen or hydroxyl and $R_5$ is hydrogen or a lower alkyl group with 1 to 4 carbon atoms, especially the methyl group.

The starting compounds used in processes (a) and (b) insofar as they are not known can be obtained, for example, in the following manner:

Process (a)

A compound of the formula

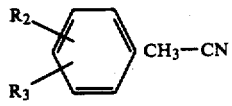

VI or

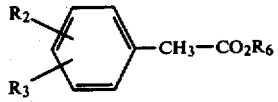

VII where $R_6$ is hydrogen or a lower alkyl group is first reacted with an active alkali compound such as sodamide, potassium amide, sodium hydride or sodium in finely divided form in an inert solvent such as dioxane, dimethyl formamide, or benzene and then there is added dropwise the calculated amount of 2,6-dichloro-3-nitropyridine dissolved in the same solvent with stirring and a nitrogen atmosphere. In many cases it is suitable to change the order of addition, for example, to add the alkali compound to a solution of the phenylacetic or benzyl cyanide derivative and 2,6-dichloro-3-nitropyridine. The generally exothermic reaction leads to the alkali salts of the compounds of formula VIII:

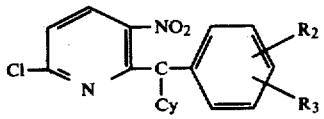

VIII where Cy is CN or $CO_2R_6$ (where $R_6$ is H or lower alkyl). Such salts are colored strongly blue to violet.

After the end of the reaction this is filtered with suction, washed, dissolved in water and treated with diluted glacial acetic acid until the disappearance of the intrinsic color. The compound of formula VIII customarily crystallizes in sufficient purity.

The 2[α-cyano)-o-chlorobenzyl]-3-nitro-6-chloropyridine is recovered, for example, as follows:

To a solution of 120 grams of o-chlorobenzyl cyanide in 1.5 liters of dioxane there were added at 45° C. with stirring in a nitrogen atmosphere 42 grams of sodium hydride (80% in white oil). Then the mixture was stirred for 45 minutes more at this temperature. The solution was then cooled and at 20° to 22° C. there were dropped in within 30 minutes 140 grams of 2,6-dichloro-3-nitropyridine in 500 ml of dioxane. Further reaction was permitted for three hours at this temperature. The deeply colored sodium salt was filtered off, washed with dioxane, dissolved in water/methanol (1:1 by volume) and diluted acetic acid added until the color changed. The desired compound crystallized out, was filtered off with suction and thoroughly washed with methanol, M.P. 174°-175° C., Yield 91 grams.

By oxidation of the compound of formula VIII there can be produced the corresponding 2-benzoyl-3-nitro-6-chloropyridine derivative (formula IX)

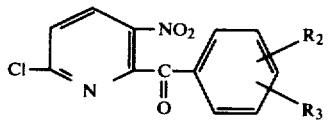

IX

This can be accomplished for example, with selenium dioxide in dioxane or tetrahydrofurane at 50° to 150° C. or can also be carried out by treating the compound of formula VIII with 30% aqueous hydrogen peroxide at temperatures below 100° C., preferably at 20° to 50° C. in acetone-water, wherein the stoichiometrical amount of an aqueous concentrated KOH solution is dropped in just rapidly enough that no change in color takes place. In the latter method there is simultaneously hydrolytically split off to a large extent the chlorine atom in the 6 position. There is also isolated therefore in addition to the desired compound of formula IX the compound wherein the 6-chloro atom is replaced by OH, i.e. $R_1$ is OH. The latter can then in known manner again be chlorinated with a mixture of $PCl_3/PCl_5$ wherein the $PCl_3$ simultaneously again deoxygenates the N-oxide formed as a byproduct. In the compounds of Formula IX the nitro group is then reduced to an amino group either catalytically (with Pd, Pt or Raney-Ni in alcohol, dioxane or tetrahydrofurane between 0° and 60° C. and 1 to 50 atmospheres absolute) or chemically (with $LiAlH_4$ or $Al/Hg/H_2O$ in ether, dioxane or tetrahydrofurane between 0° to 60° C.). This amino group can then be substituted by the $R_5$ radical by the process given in the application.

For the production of compounds of the formula X

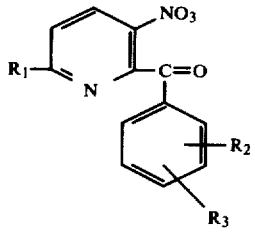

X where $R_1$ is F or Br for example, a compound of formula IX is heated with a saturated aqueous-alcoholic ammonia solution in an autoclave at 100° to 120° C. for several hours (e.g. 2 to 4 hours) and the 6-aminopyridine derivative formed thereby diazotised in known manner and reacted according to the conditions of the Sandmeyer reaction or the modified Sandmeyer reaction by heating in the presence of fluoride or bromide ions and/or the corresponding copper (I) salts (Cu Br, CuCl) or fluoborate ions, e.g. sodium fluoborate. As solvents there can be used water-alcohol mixtures, or mixtures of water, dimethyl formamide and dimethyl sulfoxide. For the production of fluorine derivatives there can also be employed the thermal decomposition of the dry diazonium fluoborate.

Compounds of formula X in which $R_1$ is a bromine atom also can be obtained by bromination of a compound of formula X in which $R_1$ is replaced by OH by using a bromination agent such as $POBr_3$, $PBr_5$ or $SOBr_2$, in a given case in an inert medium between 20° and 200° C. The production of compounds of formula X wherein $R_1$ is F can also be produced in modified manner by either gradually adding $NaNO_2$ to a solution in aqueous hydrofluoric acid of a compound of formula X wherein $R_1$ is replaced by an amino group, at temperatures between 0° and 50° C., or by introducing a slow stream of nitrous gases to such a solution.

The reduction of the nitro group as well as the subsequent introduction of $R_5$ takes place in the manner already set forth.

Compounds of formula II wherein W is the group =NH or—NOH can be obtained for example, from compounds of formula II wherein W is oxygen and the remaining symbols $R_1$, $R_3$, $R_3$ and $R_5$ have the already defined meaning by treating with ammonia or hydroxylamine. This reaction is preferably carried out in polar organic solvents (e.g. aliphatic alcohols such as those mentioned above, dioxane, tetrahydrofurane, pyridine or liquid ammonia), preferably between 0° and 150° C. as well as in a given case at pressures between 1 and 100 atmospheres absolute.

Unless otherwise indicated all parts and percentages are by weight.

EXAMPLE 1

5-Phenyl-6-aza-7-chloro-1,2-dihydro-3H-1,4-benzodiazepinone-(2)

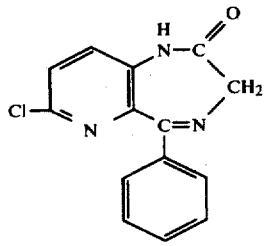

21 grams of N-benzyloxycarbonyl glycine were made into a paste in 400 ml. of dry ether and treated with stirring with 21 grams of phosphorus pentachloride. After everything was in solution there were added with stirring 23 grams of 2-benzoyl-3-amino-6-chloropyridine in 90 ml of chloroform and stirred at room temperature for 2 hours whereupon there precipitated 2-benzoyl-3-[N-(benzyloxycarbonylamino-acetyl)amino]-6-chloropyridine. It was filtered off with suction and washed with ether (Yield 30 grams, M.P. 130° C.), 105 grams of this intermediate product (obtained from several batches) was added in portions to a solution of 100 grams of hydrogen bromide in 360 ml of glacial acetic acid. There immediately was formed a paste with $CO_2$ evolution. The mixture was further stirred for one hour and to complete the development of the precipitate ether was added. The precipitate was filtered off, made into a paste in methanol and concentrated aqueous ammonia solution added whereupon the material went into solution. The thin layer chromatographic examination showed that the first formed open glycyl derivative cyclized upon the setting free of the base. After a short period of standing the solution was treated with water until turbidity developed, whereupon the material crystallized out. It was recrystallized from isopropanol. Yield 60 grams; M.P. 198° C.

Production of the Starting Material

There were gradually added to a cooled and stirred solution of 190 grams of 2,6-dichloro-3-nitropyridine and 117 grams of benzyl cyanide in 2 liters of dioxane under a nitrogen atmosphere 64 grams of sodium hydride (80% in white oil). The reaction mixture immediately turned a deep dark blue color, gradually a finely divided precipitate began to separate out, the temperature rose (with cooling with ice water) to 30° C. After 3 hours the mixture was treated with about 20 ml of ethyl alcohol, stirred for another 20 minutes, then filtered with suction. The deep blue sodium salt was dissolved in 1 liter of water, treated with dilute acetic acid until the color changed. The 2-(α-cyanobenzyl)-3-nitro-6-chloropyridine formed crystallized out in pure form. M.P. 165° C.; Yield 146 grams.

A mixture of 200 grams of 2-(α-cyanobenzyl)-3-nitro-6-chloroyridine, 500 ml of acetone and 160 ml of 30% aqueous hydrogen peroxide were treated with stirring at 35°-40° C. by dropwise addition of a concentrated potassium hydroxide solution (from 75 grams of KOH and 50 ml of water). The addition was carried out at a rate just sufficiently quick that a color change did not take place. Immediately after a permanent color change which indicated the end of the reaction, the mixture was cooled and the separating crystallized material filtered off with suction. This material (which in several runs varied between 30 and 40 grams) was 2-benzoyl-3-nitro-6-chloropyridine which was purified by recrystallization from methanol. The filtrete was acidified with dilute hydrochloric acid whereupon the 2-benzoyl-3-nitro-6-hydroxy-pyridine precipitated in an amount between 120 and 140 grams. M.P. 211° C.

This hydroxy compound was likewise converted into the desired 2-benzoyl-3-nitro-6-chloropyridine by chlorination. For this purpose 190 grams of 2-benzoyl-3-nitro-6-hydroxypyridine (from several runs) were stirred in a mixture of 200 ml of phosphorus trichloride, 500 ml of phosphorus oxychloride and 190 grams of phosphorus pentachloride for 4 hours at 72° C. Then the phosphorus halides were vaporized in a rotary evaporator, the residue taken up in 1 liter of chloroform, washed with ice water, twice with dilute soda lye and twice with water. The chloroform solution was dried, brought to dryness in a vacuum and the residue recrystallyzed from methanol. Yield 145 grams; M.P. 106° C.

110 grams of pure 2-benzoyl-3-nitro-6-chloropyridine were catalytically hydrogenated in 500 ml of dioxane at 60 atmospheres absolute and 20° C. by 30 grams of Raney-nickel. The filtered solution was concentrated to about one-third in a vacuum, cooled to 5° C., the 2-benzoyl-3-amino-6-chloropyridine which crystallized out filtered off with suction after an hour and recrystallized from ethanol. Yield 78 grams; M.P. 159° C.

EXAMPLE 2

5-Phenyl-6-aza-7-chloro-1,2-dihydro-3H-1,4-benzodiazepinone-(2)

The same compound as that prepared in example 1 was prepared in the following manner.

15 ml of bromacetyl chloride were stirred for 2 hours at room temperature with 33 grams of 2-benzoyl-3-amino-6-chloropyridine in 200 ml of dioxan with addition of 11.5 grams of pyridine. The intermediate product was filtered off with suction, washed with ether and subsequently 25 grams of the intermediate product (2-benzoyl-3-bromoacetylamino-6-chloropyridine, M.P. 130° C.; Yield 38 grams) dissolved in 900 ml of 12% methanolic ammonia solution and allowed to stand overnight. The solution was evaporated to dryness in a vacuum, the residue dissolved in 200 ml of chloroform and the solution washed with water. The dried solution was acidified with 6 normal isopropanolic hydrochloric acid and treated with gasoline until turbidity developed. The HCl salt which crystallized out was filtered off with suction after 2 hours, dissolved in methanol and the free base produced by the addition of ammonia. The free base crystallized out upon the addition of water. Yield 10 grams; M.P. 198°-200° C.

EXAMPLE 3

5-Phenyl-6-aza-7-chloro-1,2-dihydro-3H-1,4-benzodiazepinone-(2)-4-oxide.

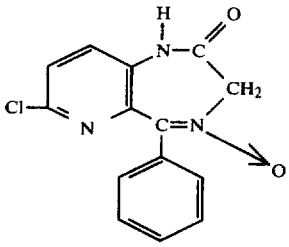

The 2-oximinobenzoyl-3-amino-6-chloropyridine (crude product) obtained from 46 grams of 2-benzoyl-3-amino-6-chloropyridine and 70 grams of hydroxylamine hydrochloride was dissolved in 400 ml of acetic acid and 32 ml of chloroacetyl chloride added. The mixture was allowed to stand for 2 days, then hydrogen chloride was led in until saturation occurred and the mixture allowed to stand for a further 3 days. The solution was evaporated to dryness in a vacuum, the residue taken up in methylene chloride and the solution thoroughly washed with water and subsequently washed with ice cold soda solution. Then it was dried with sodium sulfate and concentrated to 150 ml and petroleum ether (B.P. 40° to 70° C.) added until turbidity developed. After 2 hours the crystals of 5-aza-6-chloro-2-chloromethyl-4-phenylquinazoline-3-oxide which separated were filtered off (Yield 23 grams; M.P. 146° C.). 6.5 grams thereof were added to a mixture of 8 grams of sodium hydroxide, 20 ml of water and 100 ml of ethanol at room temperature. After several hours of standing the solution was diluted with water and weakly acidified with hydrochloric acid. The compound which crystallized out was filtered off with suction and recrystallized from ethanol. Yield 4.5 grams; M.P. 215° C.

Production of the Starting Materials

A mixture of 46 grams of 2-benzoyl-3-amino-6-chloropyridine, 15 grams hydroxylamine hydrochloride, 100 ml of pyridine and 400 ml of ethanol were heated with stirring to reflux for 6 hours. The mixture was freed of solvents whereupon the reaction product was obtained as a syrup. This was directly further worked up.

EXAMPLE 4

3-Methyl-5-phenyl-6-aza-7-chloro-1,2-dihydro-3H-1,4-benzodiazepinone-(2)

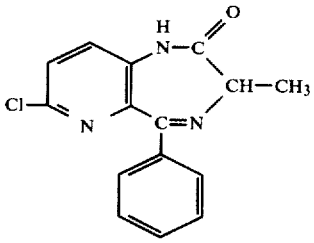

A mixture of 26 grams of 2-benzoyl-3-amino-6-chloropyridine, 28 grams of benzyloxycarbonyl-d,l-alanine, 28 grams of phosphorus pentachloride and 500 ml of ether were stirred for one hour at room temperature. Then the mixture was evaporated to dryness and the syrupy residue (50 grams) treated with a solution of 70 grams of HBr in 200 ml of glacial acetic acid and then treated as example 1. The product precipitating from the ammoniacal solution was partially cyclized and cyclization was completed by stirring for three hours in 200 ml of boiling toluene with addition of pyridine and the splitting off of water. The desired compound crystallized out the toluene solution and was crystallized from benzene-gasoline. Yield 26 grams; M.P. 182° C.

EXAMPLE 5

3-Isopropyl-5-phenyl-6-aza-7-chloro-1,2-dihydro-3H-1,4-benzodiazepinone-(2)

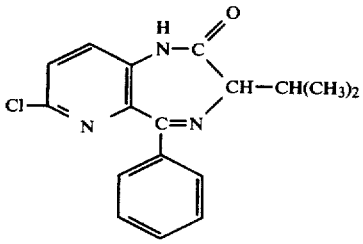

A mixture of 26 grams of 2benzoyl-3amino-6-chloropyridine, 30 grams of benzyloxycarbonyl-d,l-valine, 25 grams of phosphorus pentachloride and 400 ml of ether were stirred for an hour at room temperature. Then the mixture was evaporated to dryness and the syrupy residue (40 grams) treated with a solution of 50 grams HBr in 160 ml of glacial acetic acid and further treated in a manner analogous to example 1.

A syrupy base precipitated from the ammoniacal solution which was shown by thin layer chromatography to still contain some uncyclized precursor. This base was then cyclized by stirring for three hours in 200 ml of boiling toluene with addition of 3 ml of pyridine and the splitting off of water. The desired compound crystallized out of the toluene solution and was recrystallized from benzene-gasoline. Yield 14 grams; M.P. 225°-226° C.

EXAMPLE 6

5-(o-Chlorophenyl)-6-aza-7-chloro-1,2-dihydro-3H-1,4-benzodiazepinone-(2)

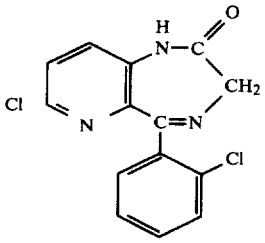

There were added 27 grams of phosphorus pentachloride in portions with stirring to a mixture of 34 grams of 2-o-chlorobenzoyl-3amino-6-chloropyridine, 27 grams of benzyloxy-carbonyl glycine and 300 ml of dioxane. The temperature rose from 27° to 37° C. The mixture was stirred further for an hour and then there were gradually added 800 ml of petroleum ether to the mixture. After seeding there crystallized out 50 grams of the 3-N-benzyloxycarbonyl intermediate. 20 grams of this product was then reacted in 70 ml of a saturated solution of HBr in glacial acetic acid and further treated as in example 1. The product precipitated from the ammoniacal solution still contained a greater amount of the open precursor and therefore was completely cyclized with the splitting off of water by stirring for three hours in 200 ml of boiling toluene with addition of 3 ml of pyridine. The pure compound crystallized out from the toluene solution. Yield 10 grams; M.P. 201° C.

EXAMPLE 7

5-(o-Chlorophenyl)-6-aza-7-chloro-1,2-dihydro-3H-1,4-benzodiazepinone-(2)-4-oxide

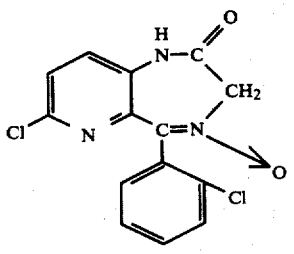

About 70 grams of 2-(o-chlorobenzoyl-oximino)-3-amino-6-chloropyridine (crude product) were dissolved in 400 ml of 99% acetic acid and 45 ml of chloroacetylchloride added. Then HCl gas was introduced whereupon gradually 2-(o-chlorobenzoyloximino)-3-chloroacetylamino-6-chloropyridine crystallized out (Yield 53 grams, M.P. 134° to 138° C.). 36 grams of this compound was then dissolved in 150 ml of 70% ethanol and 40 grams of 50% KOH added with stirring and ice bath cooling. Reaction was allowed to continue for 30 minutes at 20° C. The clear solution was acidified with acetic acid and treated with 100 ml of water. The white crystalline precipitate was filtered off with suction, washed with isopropanol and recrystallized from dioxane gasoline. Yield 14 grams; M.P. 241° to 243° C.

The oximine starting compound was obtained as follows:

A mixture of 70 grams of 2-(o-chlorobenzoyl)-3-amino-6-chloropyridine (produced in a manner analogous to that described in example 1 for preparing 2-benzoyl-3-amino-6-chloropyridine), 30 grams of hydroxylamine hydrochloride and 200 ml of pyridine were stirred for 20 hours at room temperature. An additional 30 grams of hydroxylamine. HCl were added and the mixture stirred for a further 20 hours. The pyridine was then evaporated in a rotary evaporator, the residue taken up in 200 ml of chloroform and the solution washed several times with water. The chloroform solution was briefly dried, the desired substance partially crystallized out from the drying solution. The solution was evaporated to dryness and the residue further reacted directly.

EXAMPLE 8

5-(2,5-Dichlorophenyl)-6-aza-7-chloro-1,2-dihydro-3H-1,4-benzodiazepinone-(2)

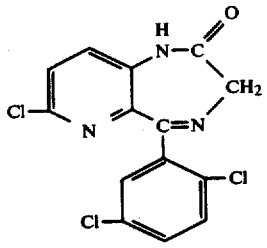

A mixture of 10 grams of 2-(2,5-dichlorobenzoyl)-3-amino-6-chloropyridine (produced in a manner analogous to that described in example 1 for preparing 2-benzoyl-3-amino-6-chloropyridine), 70 ml of dry dioxane, 10 grams of benzyloxycarbonyl glycine and 10 grams of phosphorus pentachloride were stirred for 2 hours at room temperature. Then the solvent was removed in a vacuum and the residue (14 grams) was further treated in the manner described in example 6. Yield 8 grams; M.P. 240° C.

EXAMPLE 9

1-Methyl-5-(o-fluorophenyl)-6-aza-7-chloro-1,2-dihydro-3H-1,4-benzodiazepinone-(2)

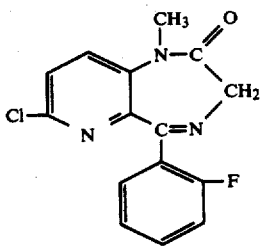

A mixture of 25 grams of 2-o-fluorobenzoyl-3-N-methylamino-6-chloropyridine (produced in a manner analogous to that described in example 1 for preparing 2-benzoyl-3-amino-6-chloropyridine), 30 grams of benzyloxycarbonyl glycine, 100 ml of dioxane and 30 grams of phosphorus pentachloride were stirred for 2 hours at room temperature. Then the solvent was removed in a vacuum and the residue (61 grams) added in portions to 500 ml of 40% HBr containing glacial acetic acid and stirred further for 1 hour. Then the reaction solution was treated with 1.5 liters of ether, the amorphous precipitate filtered off and heated with strong stirring under reflux in 500 ml of toluene and 100 ml of pyridine for 4 hours on the water trap. Then the insolubles were filtered off. The solution was evaporated to dryness in the rotary evaporator. The residue was crystallized from ethanol. Yield 22 grams; M.P. 139° C.

EXAMPLE 10

5-(-Fluorophenyl)-6-aza-7-chloro-1,2-dihydro-3H-1,4-benzodiazepinone-(2)

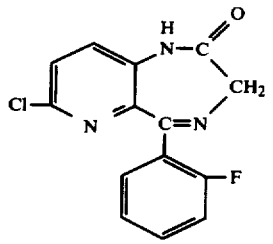

A mixture of 35 grams of 2-o-fluorobenzoyl-3-amino-6-chloropyridine (produced in a manner analogous to that described in example 1 for preparing 2-benzoyl-3-amino-6-chloropyridine), 33 grams of benzyloxycarbonyl glycine, 500 ml of ether and 33 grams of phosphorus pentachloride were stirred for 2 hours at room temperature. Then the solvent was removed in a vacuum and the residue (55 grams) further treated in a manner analogous to that described in example 6. The product obtained was recrystallized from n-propanol. Yield 28 grams; M.P. 195° to 196° C.

EXAMPLE 11

3-Benzyl-5-phenyl-6-aza-7-chloro-1,2-dihydro-3H-1,4-benzodiazepinone-(2)

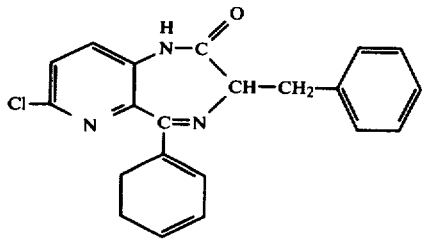

A mixture of 35 grams of d,l-carbobenzoxy phenylalanine, 400 ml of ether and 26 grams of phosphorus pentachloride were stirred for 20 minutes. To the solution there were then added 26 grams of 2-benzoyl-3-amino-6-chloropyridine and stirred for an hour at room temperature. The product which precipitated (2-benzoyl-3-[N-(benzyloxy carbonylamino-β-phenylpropionyl)-amino]-6-chloropyridine, M.P. 182° C.) was filtered off with suction and after drying (45 grams) stirred with 280 ml of 40% HBr containing glacial acetic acid and further treated in a manner analogous to example 6. Yield 28.4 grams; M.P. 234° C.

EXAMPLE 12

3-Carboxyethoxy-5-(o-chlorophenyl)-6-aza-7-chloro-1,2-dihydro-3H-benzo-1,4-diazepinone-(2)

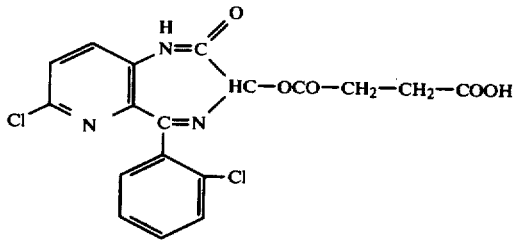

1 gram of the sodium-salt of 3-hydroxy-5-(o-chlorphenyl-)-6-aza-7-chloro-1,2-dihyro-3H-benzo-1,4-diazepinone-(2) (prepared from a ethanolic solution of the 3-hydroxy-compound by addition of an equivalent amount of sodium methylate in ethanol and precipitation of the salt by addition of ether), 0.7 grams succinic acid anhydride and 2 ml dimethylsulfoxide were heated for 20 min. on a steambath, then cooled to room temperature and 3 ml water added. The compound crystallized on seeding. Yield 0.4 grams; m.p. 170°-1° C. From the mother-liquor additional 0.4 grams of the compound could be obtained, which was purified by recrystallization from ethanol/water. Total yield of pure compound: 0.65 grams.

EXAMPLE 13

3-Hydroxy-5-o-chlorophenyl-6-aza-7-chloro-1,2-dihydro-3H-1,4-benzodiazepinone-(2)

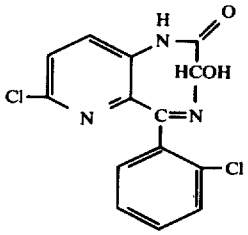

300 grams of 30% KOH were added with stirring at 15° C. to a solution of 110 grams of 1-acetyl-3-acetoxy-5-(o-chlorophenyl)-6-aza-7-chloro-3H-1,4-benzodiazepinone-(2) in 400 ml of ethanol. The mixture was stirred for 30 minutes at room temperature. The clear solution was adjusted to a pH of 5 with acetic acid and treated with 250 ml of water. The amorphous precipitate which separated was filtered off with addition of activated carbon. The filtrate was treated with 1½ liters of water and shaken with chloroform. The organic phase was dried and concentrated. The residue was recrystallized twice from ethanol. Yield 23 grams; M.P. 200° to 202° C.

EXAMPLE 14

5-Phenyl-6-aza-7-chloro-1,2-dihydro-3H-1,4-benzodiazepinone-(2)

The compound of example 1 was produced by reduction of the N-oxide as follows:

3 grams of 5-phenyl-6-aza-7-chloro-1,2-dihydro-3H-1,4-benzodiazepinone-(2)-4-oxide were hydrogenated with 5 grams of Raney nickel in 150 ml of methanol at atmospheric pressure and room temperature. The theoretical volume of hydrogen was taken up after 90 minutes. The filtered solution was evaporated to dryness in a vacuum, the residue recrystallized from ethanol. Yield 2 grams, M.P. 198° C.

EXAMPLE 15

1-Acetyl-3-acetoxy-5-(o-chlorophenyl)-6-aza-7-chloro-1,2-dihydro-3H-1,4-benzodiazepinone-(2)

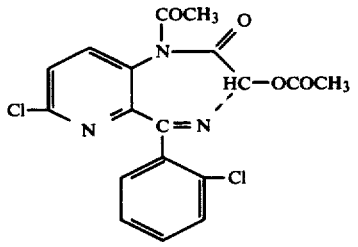

A mixture of 23 grams of 5-(o-chlorophenyl)-6-aza-7-chloro-1,2-dihydro-3H-1,4-benzodiazepinone-(2)-4-oxide and 120 ml of acetic anhydride were boiled for 30 minutes at reflux. Then it was poured into 700 ml of ice water. The substance crystallizing out was recrystallized from methanol. Yield 15 grams; M.P. 203° to 207° C.

EXAMPLE 16

3-Hydroxy-5-phenyl-6-aza-7-chloro-1,2-dihydro-3H-1,4-benzodiazepinone-(2)

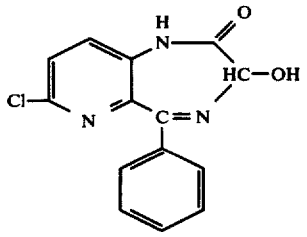

There was obtained a mixture of 1-acetyl-3-acetoxy-5-phenyl-6-aza-7-chloro-1,2-dihydro-3H-1,4-benzodiazepinone-(2) and 3-acetoxy-5-phenyl-6-aza-7-chloro-1,2-dihydro-3H-1,4-benzodiazepinone-(2) by heating 24 grams of 5-phenyl-6-aza-7-chloro-1,2-dihydro-3H-1,4-benzodiazepinone-(2)-4-oxide with 160 ml of acetic anhydride (30 minutes on the water bath) and pouring into water. This mixture was deacylated with 3 parts of 30% KOH and 4 parts of ethanol at 15° C. After acidification and dilution with water the mixture was shaken with chloroform and the chloroform residue recrystallized twice from ethanol. Yield 11 grams; M.P. 177° C.

EXAMPLE 17

1-Methyl-5-phenyl-6-aza-7-chloro-1,2-dihydro-3H-1,4-benzodiazepinone-(2)

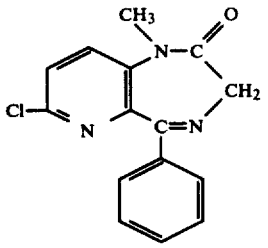

There were added portionwise under a nitrogen atmosphere with stirring 2.5 grams of sodium hydride (80% in white oil) to 20 grams of 5-phenyl-6-aza-7-chloro-1,2-dihydro-3H-1,4-benzodiazepinone-(2) in 120 ml of dry dimethyl formamide. The temperature was held at 25° C. After an hour there were added dropwise 15 grams of methyl iodide, then the mixture was stirred for 1 hour at 30° C. and 1 hour at 40° C. After standing overnight the solvent was evaporated in a vacuum, the residue taken up in methylene chloride, washed several times with water and once with dilute hydrochloric acid dried with sodium sulfate and concentrated. The residue was recrystallized from benzene-gasoline. Yield 11 grams; M.P. 154° C.

EXAMPLE 18

1-Allyl-5-phenyl-6-aza-7-chloro-1,2-dihydro-3H-1,4-benzodiazepinone-(2)

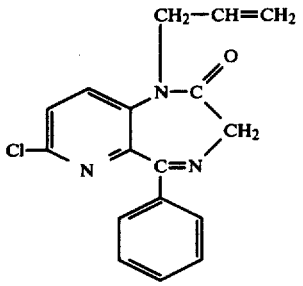

The compound was prepared in a manner analogous to example 17 using 20 grams of 5-phenyl-6-aza-7chloro-1,2-dihydro-3H-1,4-benzodiazepinone-(2) and 11 grams of allyl bromide. Yield 7 grams; M.P. 94° C.

EXAMPLE 19

1-Cyclopropylmethyl-5-phenyl-6-aza-7-chloro-1,2-dihydro-3H-1,4-benzodiazepinone 2)

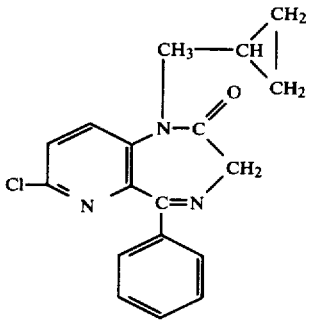

The compound was produced in a manner analogous to example 17 using 23 grams of 5-phenyl-6-aza-7-chloro-1,2-dihydro-3H-1,4-benzodiazepinone-(2) and 12 grams of cyclopropylmethyl chloride. The reaction product was purified chromatographically over an aluminum oxide column (60 cm long, 5 cm diameter, running medium chloroform), the syrup of the pure compound then dissolved in about 100 ml of ether and isopropanolic HCl (6 N) added, whereupon the hydrochloride crystallized out. Yield 5 grams; M.P. 180°-188° C.

EXAMPLE 20

1-(β-Diethylaminoethyl)-5-phenyl-6-aza-7-chloro-1,2-dihydro-3H-1,4-benzodiazepinone-(2)

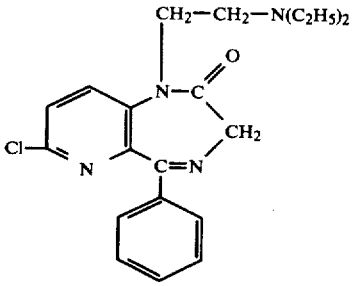

To a solution of 20 grams of 5-phenyl-6-aza-7-chloro-1,2-dihydro-3H-1,4-benzodiazepinone-(2) in 50 ml of dimethyl formamide there were added 2.5 grams of sodium hydride (80% in white oil) with stirring and under nitrogen at room temperature. The temperature was increased during 30 minutes to 50° C., then there was added dropwise a solution of 9 grams of freshly produced diethylaminoethyl chloride in 20 ml of dimethyl formamide and subsequently 0.5 grams of potassium iodide was added. The mixture was stirred for 1hour at 70° C., then concentrated to 20 ml in a vacuum and 50 ml of ethanol as well as 60 ml of water added. The substance crystallized out by trituration. It was recrystallized from benzene-gasoline. Yield 15 grams; M.P. 154° C.

EXAMPLE 21

1-Methyl-5-(o-chlorophenyl)-6-aza-7-chloro-1,2-dihydro-3H-1,4-benzodiazepinone-(2)

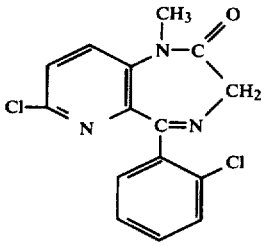

10 grams of 5-(o-chlorophenyl)-6-aza-7-chloro-1,2-dihydro-3H-1,4-benzodiazepinone-(2) were methylated with methyl iodide using a procedure analogous to that in example 17. The reaction solution was evaporated in a vacuum. The residue treated with water and benzene, the benzene layer washed twice with water, and then dried. The hydrochloride crystallized out upon the addition of 6 normal isopropanolic hydrochloric acid. This was recrystallized once from methanol-ether and once from ethanol. Yield 4 grams; M.P. 204° to 206° C. (decomposition).

EXAMPLE 22

5-Phenyl-6-aza-7-chloro-1,2-dihydro-3H-1,4-benzodiazepine

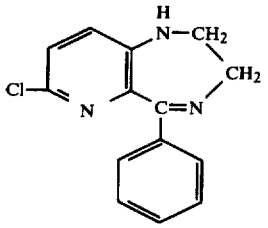

There were added dropwise with stirring inside 45 minutes 41 grams of 5-phenyl-6-aza-chloro-1,2-dihydro-3H-1,3-benzodiazepinone-(2) dissolved in 600 ml of tetrahydrofurane to a mixture of 11.5 grams of $LiAlH_4$ in 200 ml of dry tetrahydrofurane. From the initial 30° C. the temperature thereupon rose to 40° C. Then the mixture was heated to 60° C. and held at this temperature about 6 minutes, then quickly cooled to 0° to 10° C. and a mixture of 28 grams of water, 15 grams of methanol and 100 ml of tetrahydrofurane added dropwise. All of these operations were carried out under a nitrogen atmosphere. The reaction mixture was filtered, the filtrate dried with $MgSO_4$ and evaporated in a vacuum. The residue was taken up in benzene. Then 7 grams of the desired compound crystallized out of the benzene solution by standing overnight at 5° C. M.P. 161° C. To the mother liquor there was added a solution of 10 grams of malic acid in 50 ml of acetone whereupon the maleate crystallized out. The maleate was recrystallized from ethanol. M.P. 186° to 187° C. (decomposition). Yield of maleate 15 grams.

EXAMPLE 23

1-Methyl-5-phenyl-6-aza-7-chloro-1,2-dihydro-3H-1,4-benzodiazepinthione-(2)

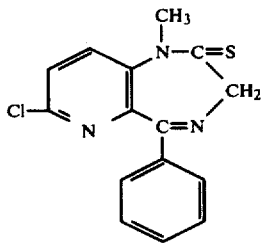

A mixture of 26 grams of 5-phenyl-6-aza-7-chloro-1,2-dihydro-3H-1,4-benzodiazepinone-(2), 32 grams of phosphorus pentasulfide and 150 ml of toluene were heated to boiling with stirring for 2 hours. Then the mixture was filtered, the solution evaporated in a vacuum, the residue combined with the filter residue and treated with a large amount of aqueous concentrated ammonia and ice. After stirring for 30 minutes it was filtered with suction. The product was dissolved in chloroform, chromatographed over an aluminum oxide column (60 cm long, 5 cm diameter, running medium chloroform) and the purified product recovered by distilling off the chloroform recrystallized from benezene. Yield 10 grams; M.P. 158° C.

EXAMPLE 24

1-Methyl-5-(o-chlorophenyl)-6-aza-7-chloro-1,2-dihydro-3H-1,4-benzodiazepinthione-(2)

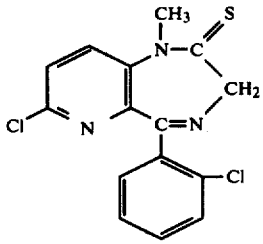

A mixture of 40 grams of 1-methyl-5-(o-chlorophenyl)-6-aza-7-chloro-1,2-dihydro-3H-1,4-benzodiazepinone-(2) and 29 grams of phosphorus pentasulfide in 200 ml toluene were reacted and worked up as in example 23. Yield 12 grams; M.P. 188° to 189° C.

EXAMPLE 25

5-Phenyl-6-aza-7-chloro-1,2-dihydro-3H-1,4-benzodiazepinthione-(2)

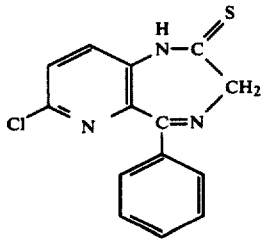

A mixture of 54 grams of 5-phenyl-6-aza-7-chloro-1,2-dihydro-3H-1,4-benzodiazpinone-(2), 44 grams of phosphorus pentasulfide and 600 ml toluene were boiled at reflux for 2.5 hours under nitrogen. The granular precipitate was filtered off with suction, agitated several times with chloroform, subsequently treated with aqueous ammonia and extracted once again with chloroform. After drying the thione crystallized out in pure form from the extract. Yield 30 grams; M.P. 202° C.

EXAMPLE 26

2-Acetohydrazino-5-phenyl-6-aza-7-chloro-3H-1,4-benzodiazepine

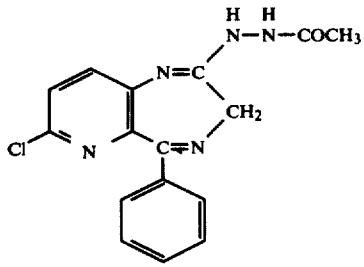

A mixture of 6 grams of acetyl hydrazine, 10 grams of 5-phenyl-6-aza-7-chloro-1,2-dihydro-3H-1,4-benzodiazepinthione-(2) and 50 ml of dioxane were heated to 50° To 60° C. for 20 minutes. The desired compound thereupon crystallized out. After cooling it was filtered off with suction and recrystallized from ethanol. Yield 10 grams; M.P. 176° C.

EXAMPLE 27

2-Methylamino-5-phenyl-6-aza-7-chloro-3H-1,4-benzodiazepine

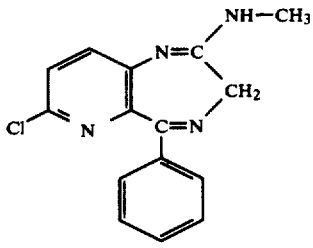

10 grams of 5-phenyl-6-aza-7-chloro-1,2-dihydro-3H-1,4-benzodiazepinthione-(2) were heated on the water bath in 200 ml of 10% methylamine solution for 10 minutes. The desired product thereupon crystallized out. It was filtered off with suction and recrystallized from benzene with the use of activated carbon. Yield 5 grams; M.P. 214° C.

EXAMPLE 28

1-Methyl-3-methoxy-5-(o-chlorophenyl)-6-aza-7-chloro-1,2-dihydro-3H-1,4-benzodiazepinone-(2)

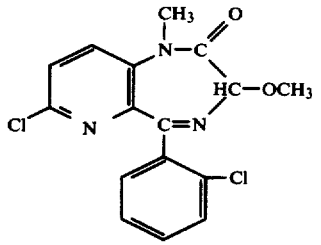

21 grams (0.065 mole) of 3-hydroxy-5-(o-chlorophenyl)-6-aza-7-chloro-1,2-dihydro-3H-benzodiazepinone-(2) were dissolved in 300 ml of dioxane and 3 ml of dimethyl formamide were added. Then there were added 4.1 grams of 80% sodium hydride in white oil and the mixture stirred for 30 minutes at room temperature. Then it was heated to 65° C., 28.4 grams (0.2 mole) of methyl iodide dropped in in 15 minutes and the mixture stirred further for one hour at this temperature. The reaction mixture was treated with 5% of acetic acid until the reaction product precipitated, the reaction product was filtered off with suction and recrystallized from ethanol. Yield 10.2 grams; M.P. 247° to 249° C.

EXAMPLE 29

1-(β-Morpholinoethyl)-5-phenyl-6-aza-7-chloro-1,2-dihydro-3H-1,4-benzodiazepinone-(2)

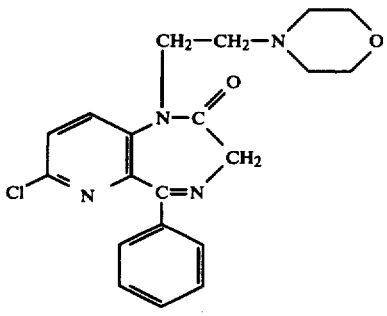

There were added at room temperature 3.5 grams of sodium hydride (80% in white oil) with stirring and under a nitrogen atmosphere to a solution of 27 grams (0.1 mole) of 5-phenyl-6-aza-7-chloro-1,2-dihydro-3,4-1,4-benzodiazepinone-(2) in 250 ml of dimethyl formamide. The mixture was stirred for 30 minutes 20 grams of N-2-chloroethyl morpholine added and heated for 2 hours at 80° to 90° C. The dimethyl formamide was drawn off in a vacuum and the residue stirred with water. The water was decanted off from the syrupy product and the latter dissolved in warm alcohol. Activated carbon was added and the product was filtered and cooled. The reaction product crystallized out. Yield: 14 grams; M.P. 162° to 164° C.

EXAMPLE 30

1-Acetyl-5-phenyl-6-aza-7-chloro-1,2-dihydro-3H-1,4-benzodiazepinone-(2)

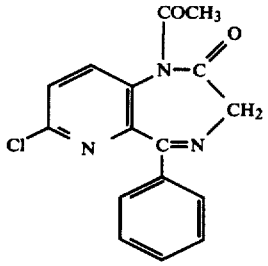

20 grams of 5-phenyl-6-aza-7-chloro-1,2-dihydro-3H-1,4-benzodiazepinone-(2) were heated for 2 hours at 120° C. in 50 ml of acetic anhydride with stirring. A white material gradually separated from the blue solution. This was filtered off with suction and recrystallized twice from dimethyl sulfoxide. Yield: 5 grams; M.P. 256° to 260° C.

EXAMPLE 31

1-β-Hydroxyethyl-5-(2-fluoro-phenyl)-6-aza-7-chloro-1,2-dihydro-3H-1,4-benzo-diazepinone-(2)

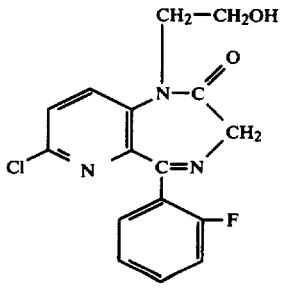

3 grams of sodium hydride (80% in white oil) were added in portions at 25° C. with stirring to a solution of 27 grams of 5-phenyl-6-aza-7-chloro-1,2-dihydro-3H-1,4-benzodiazepinone-(2) in 250 ml of dimethyl formamide. The mixture was stirred for an additional 30 minutes. Then 9 ml of bromethanol were dropped in and the mixture stirred for 7 hours at 80° to 90° C. The solvent was evaporated in a vacuum. The residue was treated with 300 ml of ether and 200 ml of 5% sodium hydroxide solution and shaken. The ether layer was washed several times with dilute soda lye and then with water. The ether solution was dried and evaporated to dryness. The crystalline residue was recrystallized twice from ethanol. M.P. 154°-156° C.

EXAMPLE 32

1-Methyl-5-(2-chlorophenyl)-6-aza-7-chloro-1,2-dihydro-3H-1,4-benzodiazepinone-(2)-4-oxide.

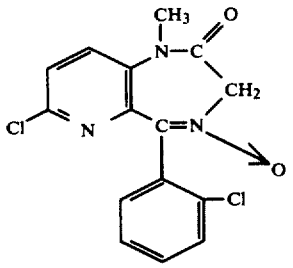

32 grams of 5-(2-chlorophenyl)-6-aza-7-chloro-1,2-dihydro-3H-1,4-benzodiazepinone-(2)-4-oxide were dissolved in a mixture of 450 ml of dioxane and 45 ml of dimethyl formamide and then 3.3 grams of NaH (80% in white oil) were added with stirring at 20° C. The temperature rose to 34° C. Then there were added dropwise 28.4 grams of methyl iodide with stirring and the mixture was stirred for 30 minutes more at 40° C. The mixture was filtered with suction, made acidic with glacial acetic acid and evaporated in a vacuum. The residue crystallized from 300 ml of ethanol upon the addition of 50 ml of gasoline. The pure material was filtered off with such and washed with ethanol. M.P. 231° C.

EXAMPLE 33

1-Methyl-3-acetoxy-5-(2-chlorophenyl)-6-aza-7-chloro-1,2-dihydro-3H-1,4-benzo-diazepinone-(2)

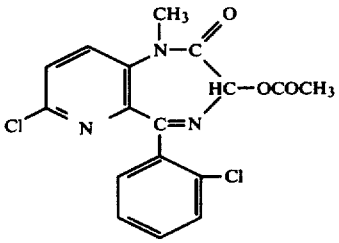

21 grams of 1-methyl-5-(2-chloro-phenyl)-6-aza-7-chloro-1,2-dihydro-3H-1,4-benzodiazepinone-(2)-4-oxide were heated for 15 minutes at the boiling point with stirring in a mixture of 33 ml of acetic anhydride and 29 ml of glacial acetic acid. After cooling and inoculation (seeding) the desired material crystallized out. It was washed with glacial acetic acid and then with water. M.P. 178° to 179° C.

EXAMPLE 34

3-Acetoxy-5-(2-chlorophenyl)-6-aza-b 7-chloro-1,2-dihydro-3H-1,4-benzodiazepinone-(2)

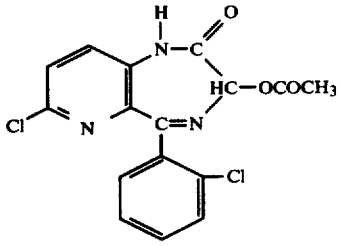

724 grams of 5-(2-chlorophenyl-6-aza-7-chloro-1,2-dihydro-3H-1,4-benzodiazepinone-(2) was introduced into a mixture of 1150 ml of acetic anhydride and 1020 ml of glacial acetic acid at 100° C. with stirring. Then the solution was heated to 120° C. An exothermic reaction took place, the mixture came to the boiling point. The reaction was finished after 15 minutes. Then the mixture was allowed to cool with stirring without applying external cooling. The material crystallized out. It was washed with water and methanol. M.P. 243° C.

EXAMPLE 35

5-(2-Fluorophenyl)-6-aza-7-chloro-1,2-dihydro-3H-1,4-benzodiazepinone-(2)-4-oxide.

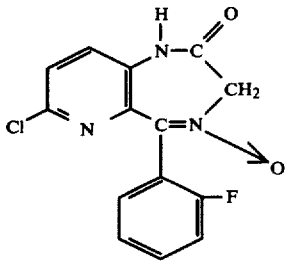

To a mixture of 166 grams of 2-(2-fluorobenzoyl)-3-chloroacetamino-6-chloropyridine oxime in 600 ml of ethanol and 300 ml of ice there were added with stirring a solution of 92.5 grams of KOH in 100 ml of water. Then the mixture was stirred for another 30 minutes and the temperature held to +5° C. by the addition of ice. The solution was filtered and 100 ml of glacial acetic acid added to the filtrate with ice cooling. The compound crystallized out. After 1 more hour of stirring it was filtered off with suction and washed with water. After recrystallization from methanol-acetone the pure compound was obtained.

EXAMPLE 36

3-Hydroxy-5-(2-fluorophenyl)-6-aza-7-chloro-1,2-dihydro-3H-1,4-benzodiazepinone-(2)

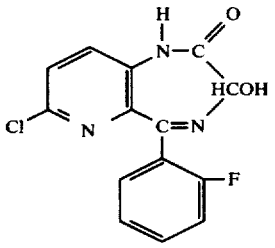

85 grams of 5-(2-fluorophenoyl)-6-aza-7-chloro-1,2-dihydro-3H-1,4-benzodiazepinone-(2)-4-oxide (crude product) were heated in 130 ml of acetic anhydride with stirring at 130° C. An exothermic reaction occurred. This was finished in 10 minutes. Thereupon the mixture was cooled and poured on ice. The precipitated material was filtered off with suction and washed with water. It consisted of a mixture of mono and diacetyl derivatives of the desired compound. 30 grams of this material (dry) were suspended in 100 ml of n-propanol. There were added in the cold (0°-5° C.) with stirring a solution of 3 grams in 40 ml of n-propanol. The mixture was treated with 700 ml of water after 15 minutes and acidified with glacial acetic acid. The desired substance crystallized out in the cooling. After standing overnight, it was filtered off with suction and recrystallized from n-propanol. M.P.: 177° to 179° C.

EXAMPLE 37

1-(β-Piperidinoethyl)-5-phenyl-6-aza-7-chloro-1,2-dihydro-3H-1,4-benzodiazepinone-(2)

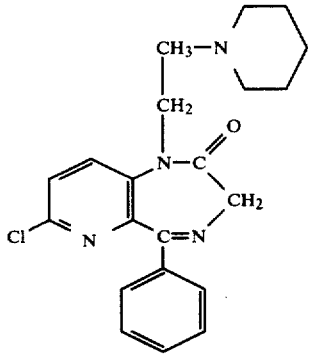

3.6 grams of sodium hydride (80% in white oil) were added to a solution of 27 grams of 5-phenyl-6-aza-7-chloro-1,2-dihydro-3H-1,4-benzodiazepinone-(2) in 250 ml of dimethyl formamide at room temperature. Then there were added at 40° C. 32 grams of piperidinoethyl chloride (freshly produced from 36.6 grams of N-chloroethylpiperidine·HCl) in a little dimethyl formamide and the mixture heated for 15 minutes at 85° to 90° C. The mixture was neutralized with glacial acetic acid and evaporated in a vacuum. The oily residue crystallized slowly by triturating with ethanol. The material was recrystallized again from ethanol with the addition of activated carbon. M.P.: 136° to 137° C.

EXAMPLE 38

5-phenyl-6-aza-7-chloro1,2-dihydro-3H-1,4-benzodiazepinone-(2)-4-oxide

The compound prepared in Example 3 was prepared as follows. 14 grams of 5-phenyl-6-aza-7-chloro-1,2-dihydro-3H-1,4-benzodiazepinone were dissolved in 250 ml of chloroform, then there were dropped in at 0° to 5° C. with stirring a solution of 11 grams of m-chloro perbenzoic acid in 150 ml of chloroform. The mixture was stirred for one hour, then allowed to stand overnight at room temperature. It was then shaken with 5% aqueous sodium hydroxide solution. This extrace was acidified with glacial acetic acid whereupon the reaction product crystallized out. It was recrystallized from ethanol. M.P. 156° to 158° C. (as monohydrate, after dehydration at 210° C.) Yield 11 grams. The compound is identical with that recovered in Example 3.

EXAMPLE 39

5-(o-chlorophenyl)-6-aza-7-chloro-1,2-dihydro-3H-1,4-benzodiazepinone-(2) (Reduction of the N-oxide)

The compound prepared in Example 6 was prepared as follows:

20 grams of 5-(o-chlorophenyl)-6-aza-7-chloro-1,2-dihydro-3H-1,4-benzodiazepinone-(2)-4-oxide in 250 ml of dioxane were hydrogenated with 5 grams of Raney-nickel at 50 atmospheres absolute and 50° C. The reaction product was precipitated from the filtered hydrogenated solution with water and recrystallized twice from n-propanol. Yield 9 grams; M.P. 200° C.

EXAMPLE 40

1-methyl-5-phenyl-6-aza-7-bromo-1,2-dihydro-3H-1,4-benzodiazepinone-(2)

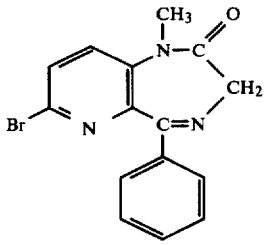

There were added with stirring at room temperature to a solution of 32 grams of 5-phenyl-6-aza-7-bromo-1,2-dihydro-3H-1,4-benzodiazepinone-(2) in 300 ml of dimethyl formamide 3.5 grams of sodium hydride (80% in white oil). After 15 minutes there were added 16 grams of methyl iodide and stirring continued for one hour at 40° C. The solution was concentrated in a vacuum to 50 ml., the residue stirred up with water and the crystalline product recrystallized from ethanol. Yield 19 grams. M.P. 148°-150° C.

EXAMPLE 41(a)

1-allyl-5-(o-chlorophenyl)-6-aza-7-chloro-1,2-dihydro-3H-1,4-benzodiazepinone-(2)

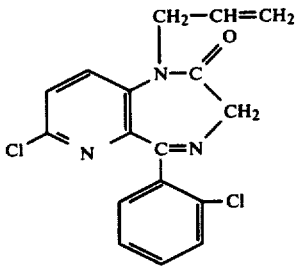

Under a nitrogen atmosphere with stirring there were added in portions at 25° C. 2.5 grams of sodium hydride (80% in white oil) to a solution of 31 grams of 5-(o-chlorophenyl)-6-aza-7-chloro-1,2-dihydro-3H-1,4-benzodiazepinone-(2) in 120 ml of dry dimethyl formamide. After 1 hour there were dropped in 10 ml of allyl bromide and the mixture stirred for 1 hour at 30° C. and then for 1 hour at 40° C. After standing overnight the solvent was removed in a vacuum, the residue taken up with methylene chloride, washed once again with water and then with dilute hydrochloric acid, dried with sodium sulfate and the solution evaporated. The reaction product thus obtained was converted into the hydrochloride by dissolving in acetone and adding isopropanolic hydrochloric acid, the hydrochloride melting at 200° to 202° C. (with decomposition) Yield 20 grams.

In an analogous way the following compounds were produced.

EXAMPLE 41(b)

1,3-Dimethyl-5-phenyl-6-aza-7-chloro-1,2-dihydro-3H-1,4-benzodiazepinone-(2)

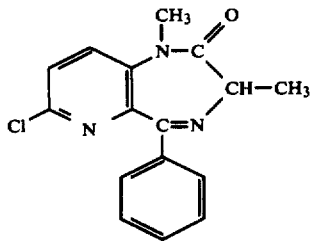

This compound was obtained from 13 grams of 3-methyl-5-phenyl-6-aza-7-chloro-1,2-dihydro-3H-1,4-benzodiazepinone-(2) and 8 grams of methyl iodide. The reaction product obtained was recrystallized from benzene-gasoline. Yield 9 grams; M.P. 132°-134° C.

EXAMPLE 41(c)

1-1,3-dimethyl-5-phenyl-6-aza-7-chloro-1,2-dihydro-3H-1,4-benzodiazepinone-(2)

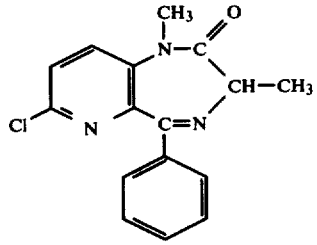

This compound was obtained from 11 grams of 1,3-methyl-5-phenyl-6-aza-7-chloro-1,2-dihydro-3H-1,4-benzodiazepinone-(2) and 8 grams of methyl iodide. The reaction product was recrystallized from benzene-gasoline. Yield 7 grams; M.P. 143°-144° C.

EXAMPLE 41(d)

1-allyl-5-(o-chlorophenyl)-6-aza-7-chloro-1,2-dihydro-3H-1,4-benzodiazepinone-(2)-oxide-(4)

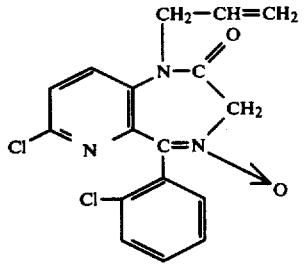

This compound was obtained from 16 grams of 5-(o-chlorophenyl)-6-aza-7-chloro-1,2-dihydro-3H-1,4-benzodiazepinone-(2)-oxide-(4) and 6.7 grams of allyl bromide. The reaction product was recrystallized from dimethyl formamide/ethanol (30:70 by volume). M.P. 220° C.; Yield 9 grams.

EXAMPLE 42

1-methyl-3-hydroxy-5-(o-chlorophenyl)-6-aza-7-chloro-1,2-dihydro-3-H-1,4-benzodiazepinone-(2)

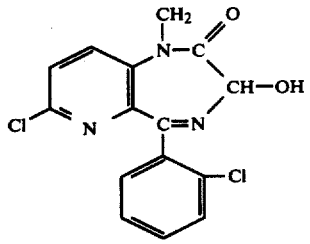

24 grams of 1-methyl-3-acetoxy-5-(o-chlorophenyl)-6-aza-7-chloro-1,2-dihydro-3H-1,4-benzodiazepinone-(2) were introduced into a solution of 1.5 grams of sodium metal in 150 ml of n-propanol and the mixture stirred at room temperature for 20 minutes. A clear solution was formed out of which a part of the product then precipitated as the sodium salt. It was acidified with glacial acetic acid and the product precipitated by the addition of 200 ml of water. The compound filtered off with suction was recrystallized from methanol. Yield 11 grams; M.P. 247°-250° C.

EXAMPLE 43

1-allyl-3-acetoxy-5-(o-chlorophenyl)-6-aza-7-chloro-1,2-dihydro-3H-1,4-benzodiazepinone-(2)

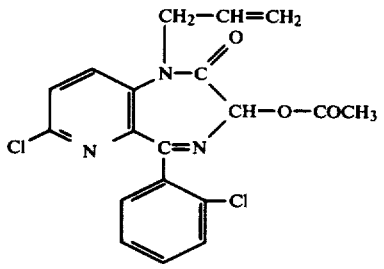

24 grams of 1-allyl-5-(o-chlorophenyl)-6-aza-7-chloro-1,2-dihydro-3H-1,4-benzodiazepinone-(2)-oxide-(4) were heated in a mixture of 29 ml of glacial acetic acid and 33 ml of acetic anhydride for 15 minutes with stirring. After cooling and innoculation the desired substance crystallized out. It was washed with glacial acetic acid and then with water. Yield 20 grams; M.P. 176°-177° C.

EXAMPLE 44(a)

5-phenyl-6-aza-7-bromo-1,2-dihydro-3H-1,4-benzodiazepinone-(2)

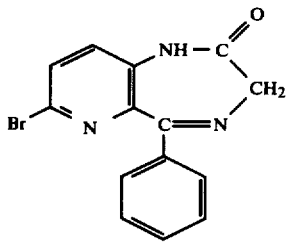

Into 200 ml of a 40% solution of hydrogen bromide in glacial acetic acid there were introduced with stirring at room temperature 43 grams of 2-benzoyl-3-[N-(benzyloxycarbonylamino-acetyl)-amino]-6-bromopyridine, whereupon brisk evolution of $CO_2$ developed. After one hour the product was precipitated with much ether and the precipitate filtered off with suction. This precipitate was stirred up with 200 ml of methanol and heated on the waterbath to boiling. Then there were added aqueous ammonia until basic reaction, whereupon a clear solution formed. After a short time of stirring the reaction product began to crystallize out; thereupon there were added 1 liter of water. After 1 hour the product was filtered off with suction, washed with water and once recrystallized out from methanol. Yield: 11 grams; M.P. 202°-204° C.

EXAMPLE 44(b)

If there is used instead of 2-benzoyl-3-(N-(benzyloxycarbonylamino-acetyl)amino]-6-bromopyridine the corresponding 6-fluoro derivative there is obtained 5-phenyl-6-aza-7-fluoro-1,2-dihydro-3H-1,4-benzodiazepinone-(2) having a M.P. of 218°-220° C. (from ethanol).

The starting material for example 44(a) was obtained as follows: 180 grams of 2-benzoyl-b 3-nitro-6-chloropyridine in a solution of 80 grams of ammonia in 1 liter of ethanol were heated in an autoclave for 5 hours to 100° to 120° C. The reaction solution was evaporated to dryness, the residue boiled with acetone, and the product precipitated from the acetone extract with water. Yield 161 grams. 50 grams of the thus obtained 2-benzoyl-3-nitro-6-aminopyridine were dissolved in 300 ml of dimethyl formamide, 125 ml of 47% aqueous hydrobromic acid added with stirring at 0° C., then there were dropped in with stirring at 0° C. a solution of 20 grams of sodium nitrate in 50 ml of water. It was stirred for one hour at room temperature and 1 hour at 60° to 70° C. Then it was poured on 2.5 liters of water, extracted with chloroform, the chloroform solution washed with aqueous sodium hydroxide and water, dried and evaporated. The residue was recrystallized from alcohol-gasoline (M.P. 98°-100° C.). 45 grams of the 2-benzoyl-3-nitro-6-bromopyridine obtained were dissolved in 450 ml of dioxane and hydrogenated on 10 grams of Raney-nickel at 50 atmospheres absolute and 60° to 70° C. The solution was filtered, concentrated to 150 ml and precipitated with water. Yield 35 grams; M.P. 146°-148° C.

In a mixture of 300 ml of choroform and 400 ml of ether there were dissolved 30 grams of N-(benzyloxycarbonyl)-glycine, then there were added with stirring 30 grams of phosphorus pentachloride. After 30 minutes stirring there were added 35 grams of 2-benzoyl-3-amino-6-bromopyridine as precedingly obtained. After one hour a flocculated precipitate was filtered off, the filtrate treated with 1 liter of gasoline, whereupon the 2-benzoyl-3-[( N-(benzyloxycarbonyl-amino-acetyl)-amino]-6-bromo-pyridine crystallized out. Yield 43 grams; M.P. 124°-126° C.

The starting material for the fluoro compound of example 44 (b) was obtained in analogous manner.

EXAMPLE 45

1-3-methyl-5-phenyl-6-aza-7-chloro-1,2-dihydro-3H-1,4-benzodiazepinone-(2)

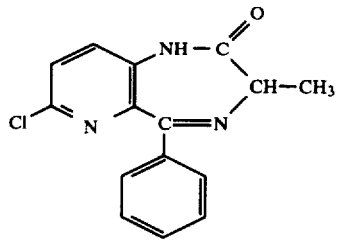

A mixture of 11.6 grams of 2-benzoyl-3-amino-6-chloropyridine, 11.15 grams of N-benzyl-oxycarbonyl-1-alanine, 12 grams of phosphorus pentachloride and 500 ml of ether were stirred for one hour at room temperature. Then the mixture was evaporated to dryness and the syrupy residue (50 grams) treated with a solution of 70 grams of HBr in 200 ml of glacial acetic acid as in Example 1. The product was further treated as in Example 1. The product precipitating from the ammoniacal solution is partially cyclized and to complete cyclization was stirred for 3 hours in 200 ml of boiling toluene. The desired compound crystallized out of the toluene solution and was recrystallized from benzene-gasoline. Yield 4.5 grams; M.P. 113°-116° C.

EXAMPLE 46

1-n-propyl-5-phenyl6-aza-7-chloro-1,2-dihydro-3H-1,4-benzodiazepinone-(2)

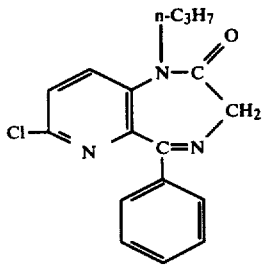

There were added with stirring at room temperature and a nitrogen atmosphere to a solution of 27.2 grams (0,1 mole) of 5-Phenyl-6-aza-7-chloro-1,2-dihydro-3H-1,4-benzodiazepinone-(2) in 200 ml of dry dioxane and 5 ml of dimethyl formamide 4,5 grams of sodium hydride (57% in white oil). The temperature rose to 30° and a clear solution was formed. This solution was warmed to 80°-85° C. and within 2 hours 25 grams of (n-)propyl bromide were dropped in. The mixture was stirred for 10 hours at 85° C. and then poured in 700 ml of water whereupon the reaction product crystallized out. It was filtered off with suction and recrystallized from methanol (two times). Yield: 17 grams. M.P. 139°-42° C.

EXAMPLE 47

1-n-butyl-5-phenyl-6-aza-7-chloro-1,2-dihydro-3H-1,4-benzodiazepinone-(2)

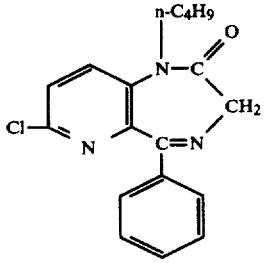

This compound was made in an analogous manner as example 46 fromm 27,2 grams of 5-phenyl-6-aza-7-chloro-1,2-dihydro-3H-1,4-benzodiazepinone-(2) and 20 grams of (n-)butyl bromide Yield: 16,5 grams. M.P. 108°-110° C.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical carriers and diluents, as well as other customary assistants.

Such carriers and assistants are set forth for example in Ullmann's Encyklopaedie die technischer Chemie, Vol. 4(1953), pages 1 to 39; Journal of Pharmaceutical Sciences, Vol. 52 (1963), pages 918 et seq; H. V. Czetsch-Lindenwald, Hilfstoffe fur Pharmazie und angrenzende Gebiete; as well as in Pharm. 2nd. Vol. 2 (1961) pages 72 et seq.; Dr. H. P. Fiedler, Lexicon der Hilfstoffe fur Pharmazie, Kosmetik und angrenzende Gebiete, Cantor Kg. Aulendorf i. Wurtt, 1971.

Examples of such materials include gelatin, sucrose, pectin, starch, tylose, talc, lycopodium, silica, lactose, cellulose derivatives, micropulverized cellulose, stearates, e.g., methylstearate, and glyceryl stearate, emulsifiers, vegetable oils, water, pharmaceutically compatible mono- or polyvalent alcohols and polyglycols such as glycerine, mannitol, sorbitol, pentacrythritol, ethyl alcohol, diethylene glycol, triethylene glycol, ethylene glycol, propylene glycol, dipropylene glycol polyethylene glycol 400, as well as derivatives of such alcohols and polyglycols, dimethyl sulfoxide, esters of saturated and unsaturated fatty acids with mono- or polyvalent alcohols such as glycols, glycerine, diethylene glycol, pentaerythritol, sorbitol, mannitol, etc., e.g., glyceryl stearate, glyceryl palmitate,glyceryl oleate, ethylene glycol stearate; such esters of polyvalent alcohols can in a given case also be etherified, benzyl benzoate, dioxolane, glycerine formal, glycol furfural, dimethyl acetamide, lactamide, lactates, e.g., ethyl lactate, ethyl carbonate, etc.

Furthermore there can be added preservatives, stabilizers, buffers, taste correctives, antioxidants and complex formers (for example ethylenediaminotetraacetic acid) and the like. In a given case for stabilization of the active molecule a pH in the range of about 5-8 can be established with physiologically compatible acids or buffers.

As antioxidants there can be used, for example, sodium meta bisulfite and ascorbic acid, as preservatives there can be used, for example, sorbic acid, p-hydroxybenzoic acid esters, e.g., methyl p-hydroxybenzoate and ethyl p-hydroxybenzoate and similar materials.

The pharmacological and galenical treatment of the compounds of the invention takes place according to the usual standard methods.

The drugs can be used enterally, parenterally, orally, perlingually or in the form of sprays.

The addition of other medicinally active materials is also desirable, especially the addition of coronary widening, spasmolytic, ulcer healing or antihypertonically effective substances.

The compounds of the invention, for example, show in combat tests on mice (spontaneous aggressiveness), as well as in electro shock and cardiazol shock methods as a good anxiolytic (tranquilizer) activity as well as a good spasmolytic activity.

The spasmolytic and anxiolytic activity is comparable to that of the known drug Diazepam.

The lowest effective dosages in animal experiments, for example, are:

1 mg/kg body weight orally (electro or cardiazole shock)

1 mg/kg body weight intravenously (combat test)

As a general range of dosage for activity (based on animal studies) there can be employed:

1-50 mg/kg body weight—orally 0.5-25 mg/kg body weight—sublingually 0.2-10 mg/kg body weight—intravenously The compounds of the invention have utility in treating emotional problems, tension, anxiety, increased irritability, psychoneurotic disturbances, vegetative dystony and organic neuroses, as well as sleep disturbances, muscle spasms (as well as illnesses of the rheumatic circulation).

The pharmaceutical preparations generally contain between 1 and 10 weight percent of the active component of the invention.

The compounds can be delivered in the form of tablets, capsules, pills, drageees, suppositories, gels, cremes, powders, liquids, dusts or aerosols. As liquids there can be used oily or aqueous solutions or suspension, emulsions, injectable aqueous or oily solutions or suspensions. The preferred forms of use are tablets which contain between 2.5 and 10 mg of active material as solutions which contain between 0.1 and 1% of active material.

In individual doses the amount of active component of the invention can be used, for example, in an amount of 5 mg dispensed orally or 0.5 mg dispensed intravenously in each case calculated as the free base. These doses can be dispensed once or several times a day.

For example, there is recommended the use of 1 to 2 tablets containing 5 mg of active ingredient 3 times daily or intravenously the injection 1 to 2 times a day of a 1 ml ampoule having 0.5 mg of active material.

The acute toxicity of the compounds of the invention in the mouse (expressed by the LD 50 mg/kg method of Miller and Tainter, Proc. Soc. Exph. Biol. and Med., Vol. 57 (1944) pages 251 et seq.) in oral application is between 800 and 2000 mg/kg (or above 800 mg/kg).

The drugs can be used in human medicine, in veterinary medicine, e.g., to treat cats, dogs, horses, sheep, cattle, goats and pigs or in agriculture. The drugs can be used alone or in admixture with other pharmacologically active materials.

The compounds of the present invention have a pronounced anxiolytic activity, i.e., they relieve or reduce anxiety. Such activity naturally cannot be measured directly in animals. However, anxiolytically active compounds exhibit anticonvulsive properties. Compounds which show marked anticonvulsive properties in animal tests, therefore, as a rule possess anxiolytic properties when used in humans. A method for testing whether a compound has anticonvulsive properties and also therewith is anxiolytically active is the Cardiazol-Shock Method.

In order to compare the therapeutic value of the compounds of the present invention with the most closely related compounds in Littell U.S. Pat. No. 3,314,941 and Reeder U.S. Pat. No. 3,371,085 tests were conducted comparing the properties of the compounds of the present application and the Littell and Reeder patents in regard to anxiolytic effect (tested by Cardiazol-Shock). The results of these tests are shown in the following table.

Furthermore, there is given in this table the ataxic activity. The ratio of ataxic activity to the anxiolytic activity is of the greatest significance in using a material as an anxiolytic agent. This quotient should be as large as possible since an ataxic activity is undesirable. Ataxic activity means that the coordination of the muscular movements is disturbed—ataxic disturbance of the muscular coordination. This means at the dosage at which a marked anxiolytic acitvity is present there should not be found a noteworthy ataxice. The toxicity, in case the data exists above the ataxic activity, is no longer important since the amount which is toxic is always considerably higher than the amount at which 50% ($ED_{50}$) of the animals have an ataxic effect. The ataxic effect was measured on mice on the pattern of the rotating rod.

TABLE

| Ex. | Anticonvulsive Activity at Cardiazol Shock $ED_{50}$ mg/kg Orally | Ataxic Activity on the Rotating Rod $ED_{50}$ mg/kg Orally | $ED_{50}$ Rotating Rod / $ED_{50}$ Card. Shock |
|---|---|---|---|
| 1 + 2 | 6.3 | 72.0 | 11.4 |
| 4 | 18.0 | 78.0 | 4.3 |
| 6 | 2.72 | 45.0 | 16.5 |
| 9 | 1.58 | 9.7 | 6.1 |
| 10 | 1.63 | 17.0 | 10.4 |
| 12 | 7.4 | 100.0 | 13.5 |
| 13 | 2.4 | 36.0 | 15.0 |
| 15 | 15.0 | 100.0 | 6.7 |
| 17 | 4.2 | 26.0 | 6.2 |
| 18 | 11.0 | 90.0 | 8.2 |
| 19 | 9.75 | 75.0 | 7.7 |
| 21 | 0.98 | 10.0 | 10.2 |
| 24 | 3.3 | 39.0 | 12.5 |
| Ex. 17 of Littell | no activity up to 1000 | 143.0 | 0.143 |
| Ex. 15 of Reeder | 1.8 | 2.7 | 1.5 |
| Ex. 34 of Reeder | 1.2 | 2.5 | 2.2 |

The Cardiazol shock procedure was carried out according to the method of F. M. Berger et al in J. Pharmacol. Exper. Therap. Vol. 116, pages 337–342 (1956). With mice the subcutaneous injection of 150 mg/kg of Cardiazol first results in short lasting spasms, then long lasting and strong spasms and finally results in the death of all of the animals within 10 to 15 minutes. By the oral administration of the anticonvulsive acting test materials at various dosages one hour prior to the administration of the Cardiazol, the 100% lethal effect of the Cardiazol is reduced depending on the dosage. From the percentage of surviving animals in the individual test groups there was plotted graphically the dosage-effect line and from this the $ED_{50}$ value was ascertained. $ED_{50}$ is the dosage at which 50% of the tested animals exhibited a marked anticonvulsive effect;

In the rotating rod test the animals (mice) were firest placed on a rotating rod 15 minutes after the application of the test material and then were placed on the rotating rod every 15 minutes and the animals which fell down within 2 minutes measured positive. From the number of animals which fell down expressed in percent there were drawn time-effect curves and the areas defined by it entered as percent effect in a probability network, the dosage-effect-line prepared and the $ED_{50}$ read off. The $ED_{50}$ mg/kg body weight of the mouse again specifies the dosage at which 50% of all the animals show a typical ataxic effect.

The compounds of the present invention which have a halogen atom attached to a pyridine ring are considerably different in properties from corresponding compounds having a halogen atom on a benzene ring in place of the pyridine ring. This can be seen for example in the comparison with the compounds of Reeder Examples 15 and 34 set forth in the Table above. In fact, the effect of replacing a benzene ring by a pyridine ring in benzodiazepines cannot be predicted.

Furthermore, it is known that a chlorine atom attached to a pyridine ring has a different effect than a chlorine atom attached to a benzene ring. Thus, the chemical characteristics are completely different.

Thus, a chlorine atom in the alpha position of a pyridine ring has the character of an acid chloride, specifically a carboxylic acid imide chloride. A carboxylic acid imide chloride has the following structure:

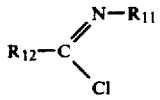

It can be seen that this same structural characteristic is true for a chlorine in the alpha position of a pyridine ring. Halogen atoms, e.g., chlorine, which are present on such compounds are easily exchanged by other substituents, see Klages "Lehrbuch der organischen Chemie", Vol. I, one half page 367 (1959) and Vol. I, 2 half page 905 (1959).

In contrast, a halogen attached to a benzene ring belongs to the most resistant substituents and only is exchangeable at high temperatures (250° C.) and in the presence of a catalyst.

Generally, a chlorine atom on a benzene ring and a chlorine atom in the alpha position of a pyridine ring are not comparable chemically. For this reason alone there can be no prediction of comparable or similar pharmacological effect.

Nieschulz et al, Arzneimittelforschung, Vol. 7, pages 113-117 (1957) shows that in 4 different N-methyl-piperidyl-methyl-chlorophenthiazine derivatives the chlorination in a benzene ring of the phenthiazine nucleus leads to a weakening on the pharmacological activity and lowering of the toxicity.

Fellows et al, Proc. Intern. Symposium on Psychotropic Drugs, Elsevier Publ. Co., Amerstom (1957), pages 397-404, on page 401 states:

"It is very interesting, however, to note that the addition of a chlorine atom to promethazine does not bring about an increase in potency as is the case when promazine is chlorinated."

In both cases the chlorine atom in question was added on a benzene ring rather than on the heterocyclic ring. In fact, Fellows points out that chlorination of promethazine not only fails to increase the potency of conditioned response blocking action, but instead results in a decrease in activity to one-half that of promethazine.

Werle et al., Arzneimittelforschung, Vol. 12, pages 443-444 shows that chlorination of certain diazophenothiazines resulted in decrease of the antihistamic activity to 1/10 that of the basic compound or even less.

Chlorpromazine

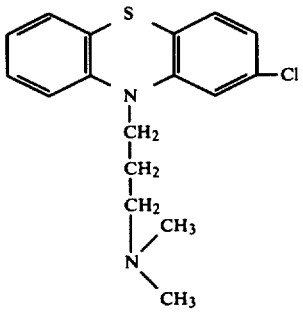

is psychotropic and used commercially as a neuroleptic. The corresponding compound without chlorine and which instead of the straight chain propylene group has an isopropylene group, namely, prometazine, on the contrary is used commercially as an antihistamine. Chlorpromazine has practically no antihistamine activity and is not used as an antihistamine.

Cyclizine (1-benzhydryl-4-methyl-piperazine) is used in the treatment of emotional illnesses and as an antiemetic; however, it is not used as an antihistamine. Chlorocyclizine (in which one hydrogen of the benzene nucleus of the cyclizine in the p-position is replaced by chlorine) on the contrary is used only as an antihistamine. If a second chlorine atom is introduced in the 2 or 3 position in the benzhydryl ring there are formed less effective compounds than chlorcyclizine.

Benadryl

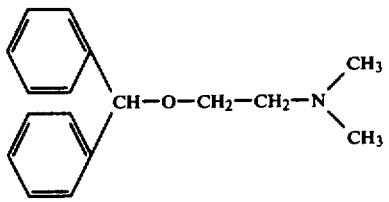

is used as an antihistamine in various allergic illnesses. The closely related chlorphenoxamine by the introduction of a p-chlorine atom and a methyl group in the alpha-position has its antihistamine activity reduced and simultaneously a strengthening of its anticholinergic activity to such an extent that it is indicated for the symptomatic treatment in all cases of Parkinsonism, J. Amer. Med. Ass. Vol. 170 (1959), pages 37 et seq.

Votava et al., First Int. Pharmacological Meeting, Vol. 8, pages 143-148 shows that in compounds of the structure

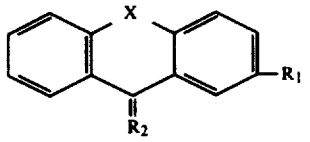

$X = -CH_2-CH_2-, -CH=CH-$ $R_1 = H, Cl, CH_3$

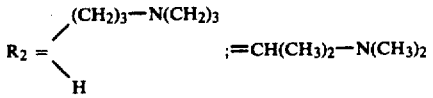

the influence of chlorine was investigated. The results were that the toxicity was raised in some cases and lowered in others and in several cases the chlorinated compounds were more effective and in other cases less effective.

The First Int. Pharmacological Meeting, Vol. 7, pages 311 et seq. shows that alpha phenyl-ethyl hydrazine has strong stimulating activity. If a hydrogen in the phenyl nucleus is replaced by chlorine, the stimulating effect is reduced and by substitut ion of two chlorine atoms there occurs in place of an antidepressive action a strong sedative action.

Thus, it is evident that pharmacological action cannot be predicted when a chlorine atom replaces a hydrogen atom on an aromatic or heterocyclic ring.

The compounds of the present invention are mainly employed orally. Thus, they are threatened with enzyme decomposition through the enzymes found there.

Also, further along the path through the intestine there are considerable possibilities for degradation (alkaline medium of the intestinal juices, enzymes and bacteria). Moreover, it could not be predicted that the substances would be unchanged over the blood flow to the place where activity occurs. Then in the passage through the liver which is an organ that manufactures extremely active substance changing materials it is possible that a large part of the acitve material is broken down or destroyed. The chemical constitution of the compounds determines whether this occurs. It could not be foreseen that a 6-aza-benzodiazepine ring compound having a halogen atom, e.g., chlorine, in the alpha position would be resistant to all of these influences and have the anticonvulsive activity and ataxic activity by oral application as shown in the preceding table.

What is claimed is:

1. A compound of the formula:

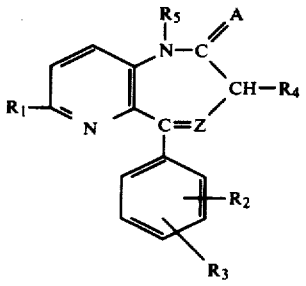

or its tautomer of the formula:

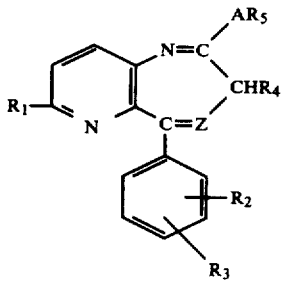

where $R_1$ is a halogen, $R_2$ and $R_3$ are hydrogen, halogen, trifluoromethyl, nitro, nitrile, hydroxy, lower alkyl or lower alkoxy, $R_4$ is hydrogen, hydroxyl, hydroxyl acylated with an alkanoic acid of 2 to 6 carbon atoms or an alkandioic acid of 3 to 6 carbon atoms, lower alkoxy, lower alkyl, benzyl, carboxyl or carb-lower alkoxy, Z is nitrogen or NO, $R_5$ is hydrogen, lower alkyl, lower alkyl substituted with cycloalkyl of 3 to 6 carbon atoms, lower alkenyl, cycloalkyl of 3 to 6 carbon atoms, hydroxy lower alkyl, benzyl, acyl of alkanoic acid of 2 to 6 carbon atoms, aminoalkyl of 2 to 7 carbon atoms, mono or di lower alkyl substituted aminoalkyl of 2 to 7 carbon atoms, lower alkyl substituted with morpholino or piperidino, and A is oxygen, sulfur, or two hydrogen atoms or in the tautomeric form —NHNHCOCH$_3$, —NHCH$_3$, —OR$_5$ or O—SR$_5$ and pharmacologically acceptable salts thereof.

2. A compound according to claim 1, where $R_4$ is hydrogen, hydroxyl, hydroxyl acylated with an alkanoic acid of 2 to 6 carbon atoms or an alkandioic acid of 3 to 6 carbon atoms, lower alkoxy, lower alkyl, carboxyl or lower carabalkoxy, $R_5$ is hydrogen, lower alkyl, lower alkyl substituted with cycloalkyl of 3 to 6 carbon atoms, lower alkenyl, cycloalkyl of 3 to 6 carbon atoms, aliphatic acyl of an alkanoic acid of 2 to 6 carbon atoms, hydroxy lower alkyl, benzyl, aminoalkyl of 2 to 7 carbon atoms, mono or di lower alkyl substituted aminoalkyl of 2 to 7 carbon atoms, lower alkyl substituted with the morpholino or piperidino ring and pharmacologically acceptable salts thereof.

3. A compound according to claim 1, where $R_5$ is hydrogen, lower alkyl, lower alkyl substituted with cycloalkyl of 3 to 6 carbon atoms, lower alkenyl, cycloalkyl of 3 to 6 carbon atoms, hydroxy lower alkyl, benzyl, acyl of an alkanoic acid of 2 to 6 carbon atoms, aminoalkyl of 2 to 7 carbon atoms, mono or di lower alkyl substituted aminoalkyl of 2 to 7 carbon atoms, lower alkyl substituted with morpholino or piperidino.

4. A compound accoding to claim 1 wherein any halogen present has an atomic weight of 9 to 80.

5. A compound according to claim 4 wherein $R_1$ is chlorine.

6. A compound accoding to claim 5, wherein $R_2$ and $R_3$ are hydrogen, fluorine or chlorine, A is O, Z is N, $R_4$ is H or OH and $R_5$ is H or alkyl of 1 to 4 carbon atoms.

7. A compound according to claim 6 wherein $R_2$ and $R_3$ are both hydrogen.

8. A compound according to claim 6 wherein $R_2$ is hydrogen and $R_3$ is fluorine or chlorine.

9. A compound according to claim 8 wherein $R_3$ is in the ortho position.

10. A compound according to claim 6 wherein $R_5$ is hydrogen.

11. A compound according to claim 6, wherein $R_5$ is methyl.

12. A compound according to claim 4 wherein $R_2$ and $R_3$ are hydrogen or halogen, $R_4$ is hydrogen, lower alkyl, benzyl, OH, hydroxy acylated with an alkanoic acid of 2 to 6 carbon atoms or an alkanedioic of 3 to 6 atoms or lower alkoxy, $R_5$ is hydrogen, lower alkyl, lower alkyl substituted with cycloalkyl of 3 to 6 carbon atoms, lower alkenyl, acyl of an alkanoic acid of 2 to 6 carbon atoms, mono or di lower alkyl substituted aminoalkyl of 2 to 7 carbon atoms, lower alkyl substituted with morpholino or piperidino through the nitrogen atom, or hydroxy lower alkyl and A is O or S or in the tautomeric form is —NHNHCOCH$_3$ or —NHCH$_3$.

13. A compound according to claim 12, wherein A is O.

14. A compound according to claim 12, wherein $R_4$ is hydrogen, lower alkyl, benzyl, OH, or hydroxy acylated with an alkanoic acid of 2 to 6 carbon atoms or an alkanedioic acid of 3 to 6 carbon atoms and $R_5$ is hydrogen, lower alkyl, lower alkyl substituted with cycloalkyl of 3 to 6 carbon atoms, lower alkenyl, or acyl of an alkanoic acid of 2 to 6 carbon atoms.

*15. A Compound according to claim 1 which is 3-hydroxy-5-o-chlorophenyl-6-aza-7-chloro-1, 2-dihydro-3H-1, 4-Benzodiazepinone-(2).*

* * * * *